US009896462B1

(12) United States Patent
Ma et al.

(10) Patent No.: US 9,896,462 B1
(45) Date of Patent: Feb. 20, 2018

(54) METAL HALIDE PEROVSKITES, METHODS, AND DEVICES

(71) Applicant: Florida State University Research Foundation, Inc., Tallahassee, FL (US)

(72) Inventors: Biwu Ma, Tallahassee, FL (US); Chenkun Zhou, Tallahassee, FL (US); Zhao Yuan, Tallhassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/270,259

(22) Filed: Sep. 20, 2016

(51) Int. Cl.
*C07F 7/22* (2006.01)
*C09K 11/06* (2006.01)
*H01L 51/00* (2006.01)
*H01L 51/50* (2006.01)
*C30B 7/14* (2006.01)
*C30B 29/22* (2006.01)

(52) U.S. Cl.
CPC ............ *C07F 7/2216* (2013.01); *C09K 11/06* (2013.01); *C30B 7/14* (2013.01); *C30B 29/22* (2013.01); *H01L 51/005* (2013.01); *H01L 51/502* (2013.01); *C09K 2211/10* (2013.01)

(58) Field of Classification Search
USPC .............................................. 556/81, 88, 95
See application file for complete search history.

(56) References Cited

U.S. PATENT DOCUMENTS 7,897,987 B2 * 3/2011 Inoue .................... H01L 33/504
257/100

FOREIGN PATENT DOCUMENTS

GB            2527796 A  *  7/2014  ......... H01L 31/0232

OTHER PUBLICATIONS

Cortecchia et al., "Polaron Self Localization in White-Light Emitting Hybrid Perovskites," arXiv:1603.01284, 2016, 34 pages.
Dohner et al., "Intrinsic White-Light Emission from Layered Hybrid Perovskites," J Am Chem Soc, 2014, 136:13154-13157.
Dohner et al., "Self-Asembly of Broadband White-Light Emitters," J Am Chem Soc, 2014, 136:1718-1721.
Dou et al., "Atomically Thin Two-Dimensional Organic-Inorganic Hybrid Perovskites," Science, 2015, 349(6255):1518-1521.
Gonzalez-Carrero et al., "Organometal Halide Perovskites: Bulk Low-Dimension Materials and Nanoparticles," Part. Part. Syst. Charact., 2015, 32:709-720.
Hao et al., "Lead-Free Solid-State Organic-Inorganic Halide Perovskite Solar Cells," Nature Photonics, 2014, 8:489-494.
Hu et al., "Mechanism for Broadband White-Light Emission from Two-Dimensional (110) Hybrid Perovskites," J Phys Chem Lett, 2016, 7:2258-2263.
Jellicoe et al., "Synthesis and Optical Properties of Lead-Free Cesium Tin Halide Perovskite Nanocrystals," J Am Chem Soc, 2016, 138:2941-2944.
Kojima et al., "Organometal Halide Perovskites as Visible-Light Sensitizers for Photovoltaic Cells," J Am Chem Soc, 131:6050-6051.
Ling et al., "Bright Light-Emitting Diodes Based on Organometal Halide Perovskite Nanoplatelets," Adv Mater, 2016, 28:305-311.
Mitzi "Templating and Structural Engineering in Organic-Inorganic Perovskites," J Chem Soc, Salton Tarns, 2001, pp. 1-12.
Noel et al., "Lead-Free Organic-Inorganic Tin Halid Perovskites for Photovoltaic Applications," Energy Environ Sci, 2014, 7:3061-3068.
Park et al., "Bismuth Based Hybrid Perovskites A3Bi2I9 (A: Methylammonium or Cesium) for Solar Cell Application," Adv Mater, 2015, 27:6806-6813.
Peedikakkandy et al., "Composition Dependent Optical, Structural and Photoluminescence Characteristics of Cesium Tin Halide Perovskites," Rsc Advances, 2016, 6:19857-19860.
Protesecu et al., "Nanocrystals of Cesium Lead Halide Perovskites (CsPbX3, X=Ci, Br, and I): Novel Optoelectronic Materials Showing Bright Emission with Wide Color Gamut," Nano Lett, 2015, 15:3692-3696.
Saparov et al., "Organic-Inorganic Perovskites: Structural Versatility for Functional Materials Design," Chem Rev, 2016, 116:4558-4596.
Sichert et al., "Quantum Size Effect in Organometal Halide Perovskite Nanoplatelets," Nano Lett, 2015, 15:6521-6527.
Stranks et al., "Metal-Halide Perovskites for Photovoltaic and Light-Emitting Devices," Nat Nanotechnol, 2015, 10:391-402.
Takeoka et al., "Hydrothermal Synthesis and Structure of Zero-Dimensional Organic-Inorganic Perovskites," Chem Lett, 2005, 34:602-603.
Tan et al., "Bright Light-Emitting Diodes Based on Organometal Halide Perovskite," Nat Nanotechnol, 2014, 9:687-692.
Xing et al., "Low-Temperature Solution-Processed Wavelength-Tunable Perovskites for Lasing," Nature Materials, 2014, 13:476-480.
Yan et al., "Hybrid Metal-Organic Chalcogenide Nanowires with Electrically Conductive Inorganic Core Through diamondoid-Directed Assembly," Nature Materials, 2016 (9 pages).
Yuan et al., "Highly Luminescent Nanoscale Quasi-2D Layered Lead Bromide Perovskites with Tunable Emissions," Chem Commun, 2016, 52:3887-3890.
Dou et al., "Solution-Processed Hybrid Perovskite Photodetectors with High Detectivity," Nature Communications, Nov. 20, 2014.

\* cited by examiner

*Primary Examiner* — Pancham Bakshi
(74) *Attorney, Agent, or Firm* — Eversheds Sutherland (US) LLP

(57) ABSTRACT

Provided herein are metal halide perovskites that may have a 0D crystal structure, and may be lead free. Also provided are methods for making the metal halide perovskites, including methods for making bulk crystals or micro crystals. Devices, such as optoelectronic devices, also are provided that include one or more of the metal halide perovskites. A metal halide perovskite may be a light emitting material in the devices.

27 Claims, 12 Drawing Sheets

METAL HALIDE PEROVSKITES, METHODS, AND DEVICES

BACKGROUND

Hybrid organic-inorganic metal halide perovskites, which include a wide range of organic cations and inorganic anions, are a class of crystalline materials that can have structural tunability. By choosing appropriate organic and inorganic components, the crystallographic structures can be controlled with the inorganic metal halide octahedrons forming various crystal structures surrounded by organic moieties (see, e.g., Mitzi, D. B. *Journal of the Chemical Society-Dalton Transactions*, 1-12 (2001); Gonzalez-Carrero, S., et al. *Part Part Syst Char* 32, 709-720 (2015); and Saparov, B. et al. *Chem Rev* 116, 4558-4596 (2016)). The integration of useful functionalities of both organic and inorganic portions within a single bulk assembly can enable these materials to possess unique electronic, magnetic, and optical properties. In recent years, the use of hybrid organic-inorganic metal halide perovskites in optoelectronic devices has been explored, including photovoltaic cells (PVs), light emitting diodes (LEDs), photodetectors, and optically pumped lasers (see, e.g., Kojima, A., et al. *J Am Chem Soc* 131, 6050 (2009); Tan, Z. K. et al. *Nat Nanotechnol* 9, 687-692 (2014); Ling, Y. C. et al. *Adv Mater* 28, 305-311 (2016); Dou, L. T. et al. *Nat Commun* 5 (2014); Xing, G. C. et al. *Nature Materials* 13, 476-480 (2014); and Stranks, S. D. et al. *Nat Nanotechnol* 10, 391-402 (2015).

The chemistry of metal halide perovskites can enable band gap control and color tuning. Highly luminescent 2D, quasi-2D, and 3D perovskites have been obtained with tunable, narrow emissions, by controlling chemical composition and quantum confinement (see, e.g., Protesescu, L. et al. *Nano Lett* 15, 3692-3696 (2015); Sichert, J. A. et al. *Nano Lett* 15, 6521-6527 (2015); Dou, L. T. et al. *Science* 349, 1518-1521 (2015); and Yuan, Z. et al. *Chem Commun* 52, 3887-3890 (2016)). Broadband emissions across the entire visible spectrum have also been realized in corrugated-2D and 1D perovskites (see, e.g., Dohner, E. R., et al. *J Am Chem Soc* 136, 1718-1721 (2014); Dohner, E. R., et al. *J Am Chem Soc* 136, 13154-13157 (2014); Hu, T. et al. *J Phys Chem Lett* 7, 2258-2263 (2016); Cortecchia, D. et al. *arXiv* 1603.01284 (2016)). Color tunability and high photoluminescence quantum efficiency (PLQE) can make metal halide perovskites desirable light-emitting materials. The research regarding hybrid organic-inorganic metal halide perovskites, however, has focused on 3D and 2D structures instead of 1D and 0D structures (see, e.g., Takeoka, Y., et al. *Chem Lett* 34, 602-603 (2005)).

Also, most high performance perovskites developed to date contain lead, which is a toxic heavy metal. Therefore, the use of lead can, in some instances, present a challenge for the potential adoption of these materials because all lead-free metal halide perovskites discovered to date, such as tin and bismuth perovskites, have shown low PLQEs (see, e.g., Noel, N. K. et al. *Energ Environ Sci* 7, 3061-3068 (2014); Hao, F., et al. *Nat Photonics* 8, 489-494 (2014); Park, B. W. et al. *Adv Mater* 27, 6806 (2015); Jellicoe, T. C. et al. *J Am Chem Soc* 138, 2941-2944 (2016); and Peedikakkandy, L. et al. *Rsc Advances* 6, 19857-19860 (2016). For example, the 0D perovskite $(CH_3NH_3)_4PbI_6 \cdot 2H_2O$ is nonemissive, and has low stability under ambient conditions (Takeoka, Y., et al. *Chem Lett* 34, 602-603 (2005)).

Therefore, perovskite materials having structures other than 1D, 2D or 3D, and are stable, efficient, color tunable, lead free, and/or have a relatively high PLQE are desirable.

BRIEF SUMMARY

Provided herein are metal halide perovskites comprising a crystal having a 0D structure, and a unit cell according to formula (I), $$R_a[MX_6]X_d \qquad (I);$$

wherein R is an organic ligand; a is 2 to 8; M is a metal atom; X is a halide ion selected from Cl, Br, or I; $MX_6$ has an octahedral structure; and d is 2 to 10. In embodiments, the organic ligand is a $C_1$-$C_{20}$ hydrocarbyl substituted with at least one of a protonated primary amine, a protonated secondary amine, or a protonated tertiary amine. The metal atom may be Sn, Cu, Ge, Mn, Co, Pb, Bi, or Eu.

Also provided herein are devices, including optoelectronic devices, comprising the metal halide perovskites of formula (I). The metal halide perovskites of formula (I) may be a light emitting material in the devices, which can include a photovoltaic cell, a light emitting diode, a light emitting electrochemical cell, a photodetector, or an optically pumped laser.

Also provided herein are methods of making a metal halide perovskite according to formula (I). In one embodiment, the method comprises contacting an organic ligand halide salt with a metal halide in a liquid to form a precursor liquid, and adding a precipitant to the precursor liquid to form one or more bulk single crystals of the metal halide perovskite. Microsize crystals of the metal halide perovskites of formula (I) also may be made by contacting an organic ligand halide salt with a metal halide in a liquid to form a precursor liquid; and mixing the precursor liquid with an organic liquid to form microsize crystals of the metal halide perovskite.

DETAILED DESCRIPTION

Figure 1A:
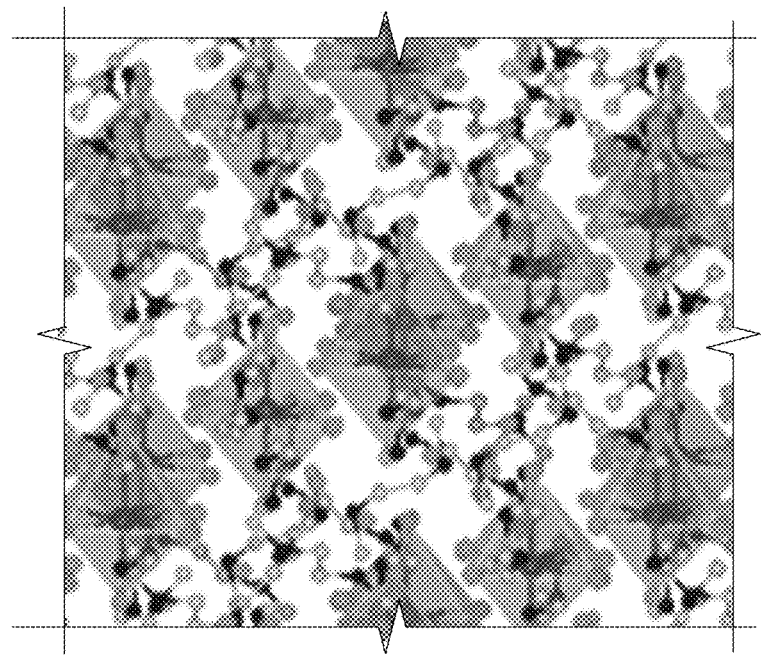
FIG. 1A depicts a crystal structure of one embodiment of a metal halide perovskite.

Provided herein are metal halide perovskites having a 0D crystal structure, including lead-free metal halide perovskites. The metal halide perovskites are stable and/or have advantageous luminescent properties, and the lead-free metal halide perovskites can be environmentally friendly. For example, the metal halide perovskites having a 0D structure may exhibit Gaussian-shaped and strongly Stokes shifted yellow emission with PLQEs of 95±5%. The metal halide perovskites, including the lead-free metal halide perovskites, may be stable in air, including at ambient temperature and pressure. The metal halide perovskites provided herein may have a bulk crystalline form or a microsize crystalline form.

In embodiments, the metal halide perovskites provided herein have a 0D structure, and a unit cell according to formula (I):

wherein R is an organic ligand; a is 2 to 8; M is a metal atom; X is a halide ion selected from Cl, Br, or I; $MX_6$ has an octahedral structure; and d is 2 to 10. The metal atom may be Sn, Cu, Ge, Mn, Co, Pb, Bi, or Eu. In one embodiment, R is an organic ligand, a is 3 to 5; M is Sn; X is Br; $MX_6$ has an octahedral structure; and d is 3 to 5. In a further embodiment, R is an organic ligand, a is 4, M is Sn; X is Br; $MX_6$ has an octahedral structure; and d is 4. In another embodiment, R is an organic ligand, a is 3 to 5; M is Sn; X is I; $MX_6$ has an octahedral structure; and d is 3 to 5. In yet another embodiment, R is an organic ligand, a is 4, M is Sn; X is I; $MX_6$ has an octahedral structure; and d is 4.

Metal Atom

The metal atom of formula (I) may be capable of forming the octahedral structure "$MX_6$", wherein X is a halide ion selected from Cl, Br, or I. The metal atom, in embodiments, is selected from Sn, Cu, Ge, Mn, Co, Pb, Bi, or Eu.

Organic Ligand

The organic ligand of formula (I) generally may have any structure that is compatible with the 0D crystal structure of the metal halide perovskites. For example, the organic ligand may include one or more positively charged moieties, such as an amine. The positively charged moieties may interact favorably with the negatively charged halide ions in the metal halide perovskites.

In one embodiment, the organic ligand is a $C_1$-$C_{20}$ hydrocarbyl or $C_6$-$C_{20}$ aryl substituted with at least one positively charged moiety, such as a positively charged amine. In a certain embodiment, the organic ligand is a $C_1$-$C_{20}$ hydrocarbyl or $C_6$-$C_{20}$ aryl substituted with two to four positively charged moieties, such as two to four positively charged amines. In a particular embodiment, the organic ligand is a $C_1$-$C_{20}$ hydrocarbyl or $C_6$-$C_{20}$ aryl that is substituted with at least one of a protonated primary amine, a protonated secondary amine, or a protonated tertiary amine. In a further embodiment, the organic ligand is a $C_1$-$C_{20}$ hydrocarbyl or $C_6$-$C_{20}$ aryl that is substituted with two to four protonated secondary amines. A protonated primary amine may have the following structure: —$NH_3^+$. A protonated secondary amine may have the following structure: —$NH_2R'^+$, wherein R' is a $C_1$-$C_{20}$ hydrocarbyl. A protonated tertiary amine may have the following structure: —$NHR''R'''^+$, wherein R'' and R''' independently are a $C_1$-$C_{20}$ hydrocarbyl.

The phrase "$C_1$-$C_{20}$ hydrocarbyl," as used herein, generally refers to aliphatic groups containing from 1 to 20 carbon atoms. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having from 1 to about 20 carbon atoms. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

The phrase "$C_6$-$C_{20}$ aryl," as used herein, refers to aryl or aromatic moieties that include from 6 to 20 carbon atoms. Examples of aryl or aromatic moieties include, but are not limited to, anthracenyl, azulenyl, biphenyl, fluorenyl, indan, indenyl, naphthyl, phenanthrenyl, phenyl, 1,2,3,4-tetrahydro-naphthalene, and the like, including substituted derivatives thereof. Substituted derivatives of aromatic compounds include, but are not limited to, tolyl, xylyl, mesityl, and the like, including any heteroatom substituted derivative thereof. Examples of cyclic groups, in each instance, include, but are not limited to, cycloparaffins, cycloolefins, cycloacetylenes, arenes such as phenyl, bicyclic groups and the like, including substituted derivatives thereof, in each instance having from about 3 to about 20 carbon atoms. Thus heteroatom-substituted cyclic groups such as furanyl are also included herein.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O— alkyl- or —OC(O)NH-alkyl), carbamyl (e.g., $CONH_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —$CCl_3$, —$CF_3$, —$C(CF_3)_3$), heteroalkyl, isocyanate, isothiocyanate, nitrile, nitro, phosphodiester, sulfide, sulfonamido (e.g., $SO_2NH_2$), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

In one embodiment of the metal halide perovskite of formula (I), the organic ligand is a $C_1$-$C_{20}$ hydrocarbyl or $C_6$-$C_{20}$ aryl substituted with at least one positively charged moiety; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is a $C_1$-$C_{20}$ hydrocarbyl or $C_6$-$C_{20}$ aryl substituted with at least one positively charged moiety, a is 4, M is Sn, Cu, Ge, Mn, Co, Pb, Bi, or Eu; X is Br or I; $MX_6$ has an octahedral structure; and d is 4. In a further embodiment, the organic ligand is a $C_1$-$C_{20}$ hydrocarbyl or $C_6$-$C_{20}$ aryl substituted with at least one positively charged moiety, a is 4, M is Sn; X is Br or I; $MX_6$ has an octahedral structure; and d is 4.

In one embodiment of the metal halide perovskite of formula (I), the organic ligand is a $C_1$-$C_{20}$ hydrocarbyl or $C_6$-$C_{20}$ aryl substituted with two positively charged moieties; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is a $C_1$-$C_{20}$ hydrocarbyl or $C_6$-$C_{20}$ aryl substituted with two positively charged moieties, a is 4, M is Sn, Cu, Ge, Mn, Co, Pb, Bi, or Eu; X is Br or I; $MX_6$ has an octahedral structure; and d is 4. In a further embodiment, the organic ligand is a $C_1$-$C_{20}$ hydrocarbyl or $C_6$-$C_{20}$ aryl substituted with two positively charged moieties, a is 4, M is Sn; X is Br or I; $MX_6$ has an octahedral structure; and d is 4.

In one embodiment of the metal halide perovskite of formula (I), the organic ligand is a $C_1$-$C_{20}$ hydrocarbyl or $C_6$-$C_{20}$ aryl substituted with at least one of a protonated primary amine, a protonated secondary amine, or a protonated tertiary amine; a is 3 to 5; M is Sn, Cu, Ge, Mn, Co, Pb, Bi, or Eu; X is Br or I; $MX_6$ has an octahedral structure; and d is 3 to 5. In another, the organic ligand is a $C_1$-$C_{20}$ hydrocarbyl or $C_6$-$C_{20}$ aryl substituted with at least one of a protonated primary amine, a protonated secondary amine, or a protonated tertiary amine; a is 4, M is Sn, Cu, Ge, Mn, Co, Pb, Bi, or Eu; X is Br or I; $MX_6$ has an octahedral structure; and d is 4. In a further embodiment, the organic ligand is a $C_1$-$C_{20}$ hydrocarbyl or $C_6$-$C_{20}$ aryl substituted with at least one of a protonated primary amine, a protonated secondary amine, or a protonated tertiary amine; a is 4, M is Sn; X is Br or I; $MX_6$ has an octahedral structure; and d is 4.

In one embodiment of the metal halide perovskite of formula (I), the organic ligand is a $C_1$-$C_{20}$ hydrocarbyl or $C_6$-$C_{20}$ aryl substituted with two protonated secondary amines; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is a $C_1$-$C_{20}$ hydrocarbyl or $C_6$-$C_{20}$ aryl substituted with two protonated secondary amines; a is 4, M is Sn, Cu, Ge, Mn, Co, Pb, Bi, or Eu; X is Br or I; $MX_6$ has an octahedral structure; and d is 4. In a further embodiment, the organic ligand is a $C_1$-$C_{20}$ hydrocarbyl or $C_6$-$C_{20}$ aryl substituted with two protonated secondary amines; a is 4, M is Sn; X is Br or I; $MX_6$ has an octahedral structure; and d is 4.

In one embodiment of the metal halide perovskite of formula (I), the organic ligand is a $C_1$-$C_{20}$ hydrocarbyl or $C_6$-$C_{20}$ aryl substituted with three protonated secondary amines; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is a $C_1$-$C_{20}$ hydrocarbyl or $C_6$-$C_{20}$ aryl substituted with three protonated secondary amines; a is 4, M is Sn, Cu, Ge, Mn, Co, Pb, Bi, or Eu; X is Br or I; $MX_6$ has an octahedral structure; and d is 4. In a further embodiment, the organic ligand is a $C_1$-$C_{20}$ hydrocarbyl or $C_6$-$C_{20}$ aryl substituted with three protonated secondary amines; a is 4, M is Sn; X is Br or I; $MX_6$ has an octahedral structure; and d is 4.

In one embodiment of the metal halide perovskite of formula (I), the organic ligand is a $C_1$-$C_{20}$ hydrocarbyl or $C_6$-$C_{20}$ aryl substituted with four protonated secondary amines; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is a $C_1$-$C_{20}$ hydrocarbyl or $C_6$-$C_{20}$ aryl substituted with four protonated secondary amines; a is 4, M is Sn, Cu, Ge, Mn, Co, Pb, Bi, or Eu; X is Br or I; $MX_6$ has an octahedral structure; and d is 4. In a further embodiment, the organic ligand is a $C_1$-$C_{20}$ hydrocarbyl or $C_6$-$C_{20}$ aryl substituted with four protonated secondary amines; a is 4, M is Sn; X is Br or I; $MX_6$ has an octahedral structure; and d is 4.

In one embodiment, the organic ligand is a compound according to the following formula (A):

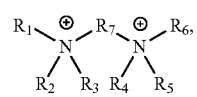

(A)

wherein each of $R_1$-$R_6$ is independently selected from hydrogen or a monovalent $C_1$-$C_{20}$ hydrocarbyl, and $R_7$ is a divalent $C_1$-$C_{20}$ hydrocarbyl or $C_6$-$C_{20}$ aryl. In another embodiment, $R_7$ is a divalent, unsubstituted $C_1$-$C_4$ hydrocarbyl, and the organic ligand is a compound according to the following formula (B):

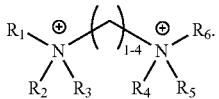

(B)

In a further embodiment, $R_7$ is a divalent, unsubstituted $C_1$-$C_4$ hydrocarbyl, each of $R_2$, $R_3$, $R_5$, and $R_6$ is hydrogen, and the organic ligand is a compound according to the following formula (C):

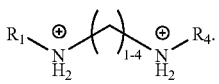

(C)

In a still further embodiment, $R_7$ is a divalent, unsubstituted $C_1$-$C_4$ hydrocarbyl, each of $R_2$, $R_3$, $R_5$, and $R_6$ is hydrogen, each of $R_1$ and $R_4$ is independently a monovalent, unsubstituted $C_1$-$C_3$ hydrocarbyl, and the organic ligand is a compound according to the following formula (D):

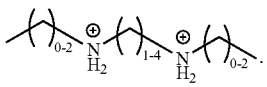

(D)

In a particular embodiment, $R_7$ is a divalent, unsubstituted $C_6$ aryl, and the organic ligand is a compound according to the following formula (E), which may be ortho-, meta-, or para-substituted:

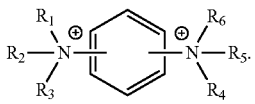

(E)

In a further embodiment, $R_7$ is a divalent, unsubstituted $C_6$ aryl, each of $R_2$, $R_3$, $R_5$, and $R_6$ are hydrogen, and the organic ligand is a compound according to the following formula (F):

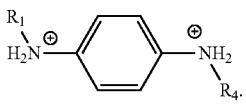

(F)

In a still further embodiment, $R_7$ is a divalent, unsubstituted $C_6$ aryl, each of $R_2$, $R_3$, $R_5$, and $R_6$ is hydrogen, each of $R_1$ and $R_4$ is independently a monovalent, unsubstituted $C_1$-$C_3$ hydrocarbyl, and the organic ligand is a compound according to the following formula (G):

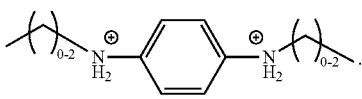

(G)

In one embodiment, the organic ligand is a compound according to the following formula (H):

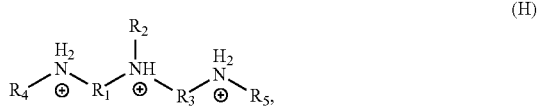

(H)

wherein each of $R_1$ and $R_3$ is independently selected from a divalent $C_1$-$C_{20}$ hydrocarbyl, and each of $R_2$, $R_4$, and $R_5$ is independently selected from hydrogen or a monovalent $C_1$-$C_{20}$ hydrocarbyl. In another embodiment, $R_2$ is hydrogen, $R_4$ and $R_5$ are independently monovalent, unsubstituted $C_1$-$C_3$ hydrocarbyls, and $R_1$ and $R_3$ are independently divalent, unsubstituted $C_2$-$C_4$ hydrocarbyls, and the organic ligand is a compound according to the following formula (I):

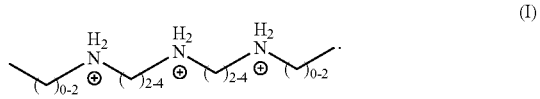

(I)

In a further embodiment, $R_2$ is a divalent, substituted $C_2$-$C_4$ hydrocarbyl, wherein the substituent is a secondary amine, $R_4$ and $R_5$ are independently monovalent, unsubstituted $C_1$-$C_3$ hydrocarbyls, and $R_1$ and $R_3$ are independently divalent, unsubstituted $C_2$-$C_4$ hydrocarbyls, and the organic ligand is a compound according to the following formula (J):

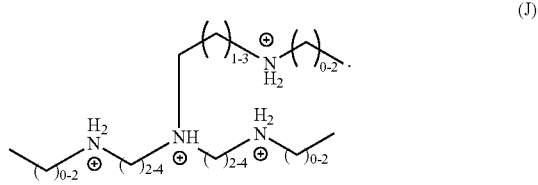

(J)

In one embodiment, the organic ligand is a compound according to the following formula (K):

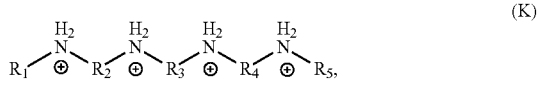

(K)

wherein $R_1$ and $R_5$ are independently selected from a monovalent $C_1$-$C_{20}$ hydrocarbyl or hydrogen, $R_2$ and $R_4$ are independently selected from a divalent $C_1$-$C_{20}$ hydrocarbyl, and $R_3$ is a divalent $C_1$-$C_{20}$ hydrocarbyl or a divalent $C_6$-$C_{20}$ aryl. In a particular embodiment, $R_1$ and $R_5$ independently are unsubstituted, monovalent $C_1$-$C_3$ hydrocarbyls, $R_2$, $R_3$, and $R_4$ are independently unsubstituted, divalent $C_2$-$C_4$ hydrocarbyls, and the organic ligand has a structure according to the following formula (L):

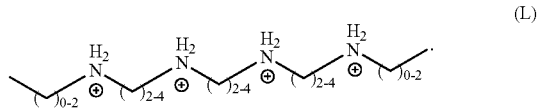

(L)

In one embodiment, the organic ligand is a compound according to the following formula (M):

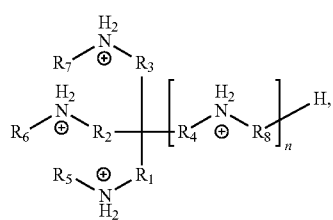
(M)

wherein n is 0 or 1, each of $R_1$-$R_4$ and $R_8$ is independently selected from a divalent $C_1$-$C_{20}$ hydrocarbyl, and each of $R_5$-$R_7$ is independently selected from a monovalent $C_1$-$C_{20}$ hydrocarbyl or hydrogen. In a particular embodiment, n is 1, $R_1$-$R_4$ independently are unsubstituted, divalent $C_1$-$C_4$ hydrocarbyls, $R_8$ is an unsubstituted, divalent $C_1$-$C_3$ hydrocarbyl, and $R_5$-$R_7$ independently are unsubstituted, monovalent $C_1$-$C_3$ hydrocarbyls, and the organic ligand is a compound according to the following formula (N):
(N).

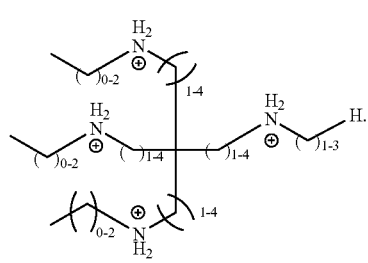
(N)

In a further embodiment, n is 0, $R_1$-$R_3$ are unsubstituted, divalent $C_1$-$C_4$ hydrocarbyls, and $R_5$-$R_7$ are unsubstituted, monovalent $C_1$-$C_3$ hydrocarbyls, and the organic ligand is a compound according to the following formula (O):

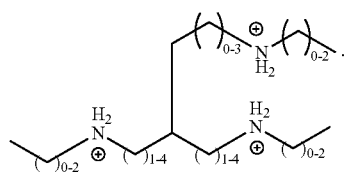
(O)

In one embodiment, the organic ligand is a compound according to the following formula (P):

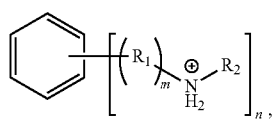
(P)

wherein m is 0 or 1, n is 1-4, each $R_1$ is independently selected from a divalent $C_1$-$C_{20}$ hydrocarbyl, and each $R_2$ is independently selected from a monovalent $C_1$-$C_{20}$ hydrocarbyl or hydrogen. In a particular embodiment, m is 0, n is 3, and $R_2$ is an unsubstituted, monovalent $C_1$-$C_3$ hydrocarbyl, and the organic ligand is a compound according to the following formula (Q):

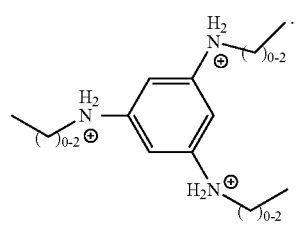
(Q)

In one embodiment of the metal halide perovskite of formula (I), the organic ligand is selected from a compound of formula (A), (B), (C), (D), (E), (F), (G), (H), (I), (J), (K), (L), (M), (N), (O), (P), (Q), or a combination thereof; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is selected from a compound of formula (A), (B), (C), (D), (E), (F), (G), (H), (I), (J), (K), (L), (M), (N), (O), (P), (Q), or a combination thereof; a is 4, M is Sn, Cu, Ge, Mn, Co, Pb, Bi, or Eu; X is Br or I; $MX_6$ has an octahedral structure; and d is 4. In a further embodiment, the organic ligand is selected from a compound of formula (A), (B), (C), (D), (E), (F), (G), (H), (I), (J), (K), (L), (M), (N), (O), (P), (Q), or a combination thereof; a is 4, M is Sn; X is Br or I; $MX_6$ has an octahedral structure; and d is 4.

In one embodiment, the organic ligand is selected from a compound according to structures (1)-(10):

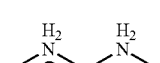
(1)

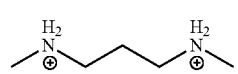
(2)

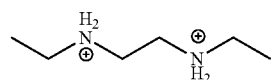
(3)

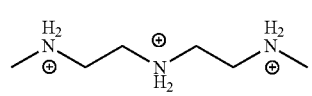
(4)

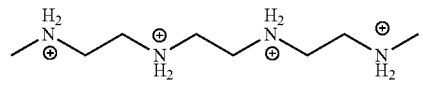
(5)

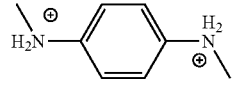
(6)

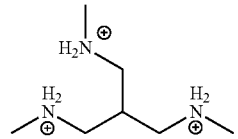
(7)

-continued

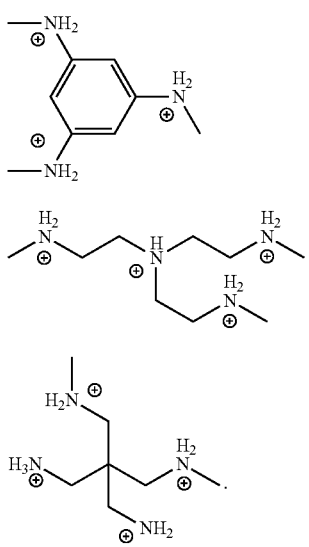

(8)

(9)

(10)

In one embodiment of the metal halide perovskite of formula (I), the organic ligand is selected from compound (1), (2), (3), (4), (5), (6), (7), (8), (9), (10), or a combination thereof; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is selected from compound (1), (2), (3), (4), (5), (6), (7), (8), (9), (10), or a combination thereof; a is 4, M is Sn, Cu, Ge, Mn, Co, Pb, Bi, or Eu; X is Br or I; $MX_6$ has an octahedral structure; and d is 4. In a further embodiment, the organic ligand is selected from compound (1), (2), (3), (4), (5), (6), (7), (8), (9), (10), or a combination thereof; a is 4, M is Sn; X is Br or I; $MX_6$ has an octahedral structure; and d is 4.

In one embodiment, the organic ligand is N,N'-dimethylethane-1,2-diammonium, which has the following structure:

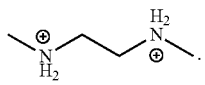

In one embodiment of the metal halide perovskite of formula (I), the organic ligand is N,N'-dimethylethane-1,2-diammonium; a is 3 to 5; M is Sn, Cu, Ge, Mn, Co, Pb, Bi, or Eu; X is Br or I; $MX_6$ has an octahedral structure; and d is 3 to 5. In another embodiment, the organic ligand is N,N'-dimethylethane-1,2-diammonium; a is 4, M is Sn, Cu, Ge, Mn, Co, Pb, Bi, or Eu; X is Br or I; $MX_6$ has an octahedral structure; and d is 4. In a further embodiment, the organic ligand is N,N'-dimethylethane-1,2-diammonium; a is 4, M is Sn; X is Br or I; $MX_6$ has an octahedral structure; d is 4; and the unit cell has the following formula: $(C_4N_2H_{14})_4[SnBr_6]Br_4$.

Crystal Size

In embodiments, the metal halide perovskites provided herein are bulk crystals. As used herein, the phrases "bulk crystals" or "bulk crystalline form" generally refer to crystals having at least one dimension that is 500 µm or greater.

In embodiments, the metal halide perovskites provided herein are micro crystals. As used herein, the phrases "micro crystals" or "microsize crystals" generally refer to crystals having an average largest dimension of about 15 µm to about 100 µm, as determined by scanning electron microscopy (SEM). In one embodiment, the micro crystals have an average largest dimension of about 15 µm to about 50 µm. The micro crystals may be a powder.

0D Structure

In embodiments, the metal halide perovskites provided herein have a 0D crystal structure. The phrases "0D crystal structure" or "0D structure," as used herein, refer to crystals having, within each unit cell, an octahedral metal halide species that is separated from one or more octahedral metal halide species of adjacent unit cells by one or more organic ligands and/or one or more halide ions.

Figure 1B:
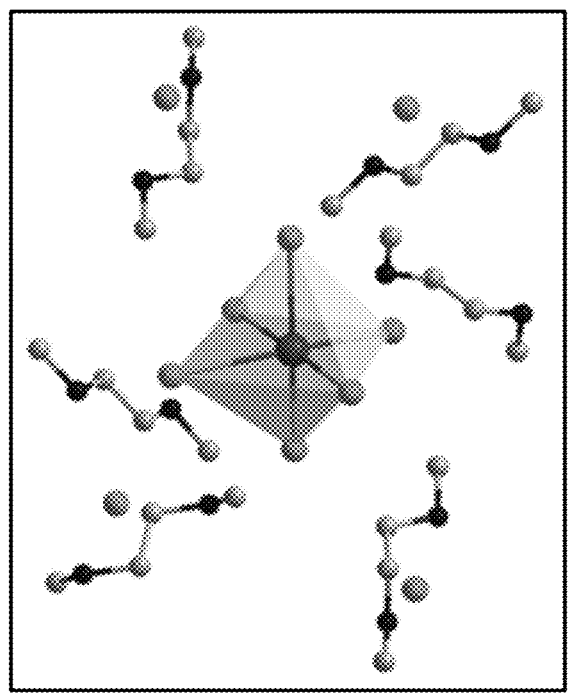
FIG. 1B depicts a single unit cell structure of the crystal of FIG. 1A.
Figure 1C:
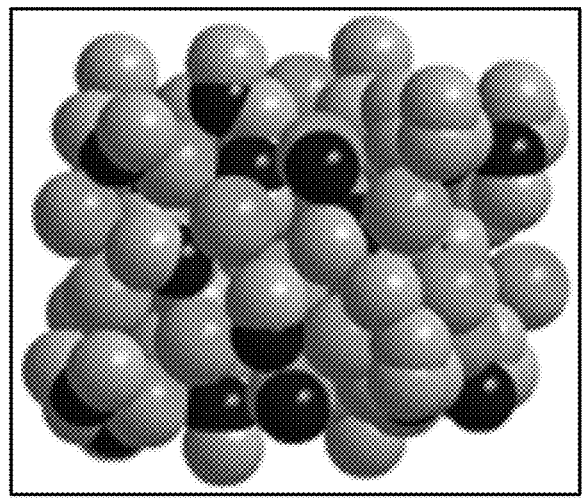
FIG. 1C is a depiction of a space filling model of one embodiment of a crystal structure with a single octahedral $MX_6$.

In one embodiment, the metal halide perovskite having a 0D structure is a tin bromide perovskite, as shown at FIG. 1A, having unit cells of the following formula: $(C_4N_2H_{14})_4SnBr_{10}$. A unit cell of this formula is depicted at FIG. 1B, which includes an individual tin bromide octahedron ($SnBr_6^{4-}$) surrounded by $C_4N_2H_{14}^{2+}$ and $Br^-$ ions. Therefore, the foregoing formula may be rewritten as $(C_4N_2H_{14})_4[SnBr_6]Br_4$. Similarly, FIG. 1C is a depiction of a space filling model of a core-shell quantum dot structure with $SnBr_6^{4-}$ completely covered by $C_4N_2H_{14}^{2+}$ and $Br^-$ ions. Therefore, as shown at FIG. 1B and FIG. 1C, the tin halide octahedral $SnBr_6^{4-}$ ions of this embodiment are completely isolated from each other and surrounded by $C_4N_2H_{14}^{2+}$ and $Br^-$ ions, which forms a bulk assembly of core-shell quantum dot like structures. Not wishing to be bound by any particular theory, it is believed that the strong quantum confinement in such a 0D structure can result in efficient exciton self-trapping that produces broadband yellow emission.

In embodiments, the metal halide perovskites provided herein achieve broadband yellow light emission with near-unity quantum efficiency at room temperature.

In one embodiment, the metal halide perovskite having a 0D structure is a tin iodide perovskite, having unit cells of the following formula: $(C_4N_2H_{14})_4SnI_{10}$.

In embodiments, the metal halide perovskites provided herein achieve broadband red light emission with near-unity quantum efficiency at room temperature.

In one embodiment, the metal halide perovskites provided herein have a PLQE of at least 90%. In another embodiment, the metal halide perovskites provided herein have a PLQE of at least 95%. In yet another embodiment, the metal halide perovskites provided herein have a PLQE of at least 98%. In a still further embodiment, the metal halide perovskites provided herein have a PLQE of at least 99%.

Methods

Methods are provided herein for making metal halide perovskites. The methods may be used to produce bulk and/or microsize crystals of the metal halide perovskites, which may have a 0D structure.

In embodiments, the methods comprise forming an organic ligand halide salt by contacting an organic ligand precursor with an acid of the formula HX, wherein X is a halogen. The halogen may be Cl, Br, or I; therefore, the acid may be HCl, HBr, HI, or any combination thereof. Any amount of acid may be used that is effective to form the organic ligand halide salt. In one embodiment, about 1.5 to about 3.0 equivalents of the acid of the formula HX is used to form the organic ligand halide salt. In another embodiment, about 2.0 to about 2.5 equivalents of the acid of the formula HX is used to form the organic ligand halide salt. In a still further embodiment, about 2.2 equivalents of the acid of the formula HX is used to form the organic ligand halide salt.

The organic ligand halide salt may be a halide salt of any of formulas (A)-(Q) or (1)-(10). In one embodiment, the organic ligand halide salt is N,N'-dimethylethane-1,2-diammonium bromide, and the organic ligand precursor is N, N'-dimethylethylenediamine. In another embodiment, the organic ligand halide salt is N,N'-dimethylethane-1,2-diammonium iodide, and the organic ligand precursor is N, N'-dimethylethylenediamine.

In embodiments, the methods provided herein comprise contacting an organic ligand halide salt with a metal halide in a liquid to form a precursor liquid; and adding a precipitant to the precursor solution to form one or more bulk single crystals of the metal halide perovskite. The metal halide and the organic ligand halide salt may be present in the precursor liquid at a molar ratio of about 1:2 to about 1:6; about 1:3 to about 1:5, or about 1:4. The liquid generally may be any liquid capable of facilitating crystal formation, especially upon addition of the precipitant. In one embodiment, the liquid is a polar organic solvent, such as dimethylformamide (DMF), dimethyl sulfoxide (DMSO), γ-butyrolactone (GBL). In a particular embodiment, the liquid is dimethylformamide (DMF). The precipitant may be any liquid capable of facilitating crystallization from the precursor liquid. In a particular embodiment, the precipitant is dichloromethane (DCM). Other liquids and precipitants are envisioned. The precipitant may be added to the precursor liquid at room temperature. The precipitant may be added over a period of about 5 to 12 hours. The bulk crystals may be produced at a yield of at least 50%, at least 60%, or at least 70%.

In embodiments, the methods provided herein comprise contacting an organic ligand halide salt with a metal halide in a liquid to form a precursor liquid; and mixing the precursor liquid with an organic liquid, such as toluene, to form micro crystals of the metal halide perovskite. The metal halide and the organic ligand halide salt may be present in the precursor liquid at a molar ratio of about 1:2 to about 1:6; about 1:3 to about 1:5, or about 1:4. The liquid generally may be any liquid capable of facilitating crystal formation, especially upon addition of the precursor liquid to the organic liquid. In one embodiment, the liquid is a polar organic solvent, such as dimethylformamide (DMF). Stirring may be used to facilitate micro crystal formation upon, during, and/or after addition of the precursor liquid to the organic liquid. In a particular embodiment, the volume ratio of precursor liquid to organic liquid, upon complete addition of the precursor liquid to the organic liquid, is about 1:2 to about 1:6, from about 1:3 to about 1:5, or about 1:4. The precursor liquid and the organic liquid may be combined in an inert atmosphere, such as in a nitrogen glove box. The micro crystals may be produced at a yield of at least about 50%, at least 60%, at least 70%, or at least 80%.

In embodiments, the metal halide used in the methods provided herein is tin(II) bromide. In another embodiment, the metal halide used in the methods provided herein is bismuth(III) bromide. In a further embodiment, the metal halide used in the methods provided herein is tin(II) iodide.

Devices

Provided herein are devices that include one or more metal halide perovskites. The metal halide perovskites provided herein, in embodiments, are light emitting materials in the devices. The metal halide perovskites may emit light that is blue, green, yellow, orange, or red. Not wishing to be bound by any particular theory, it is believed that the color emitted by the metal halide perovskites provided herein can be changed or tuned by changing the metal atom, the halide ion, the organic ligand, or a combination thereof.

In embodiments, the devices comprise at least two metal halide perovskites that emit light of different colors. For example, the devices may include a first metal halide perovskite that emits blue light, and a second metal halide perovskite that emits red light. As a further example, the devices may include a first metal halide perovskite that emits blue light, a second metal halide perovskite that emits red light, and a third metal halide perovskite that emits green light. In certain embodiments, the devices herein include full color displays. The full color display may be provided by two or more metal halide perovskites that emit light of different colors; or, alternatively, the full color display may be provided by a combination of one or more metal halide perovskites and one or more other materials, each of the materials and one or more metal halide perovskites emitting different colors of light.

The devices include optoelectronic devices, such as a photovoltaic cell, a light emitting diode, a light emitting electrochemical cell, a photodetector, and an optically pumped laser. In embodiments, the devices provided herein are solid-state lighting devices.

In embodiments, a metal halide perovskite is a yellow phosphor in the devices provided herein. The yellow phosphor may be mixed with one or more other phosphors, which may be of different colors. For example, in one embodiment, the devices include one or more of the metal halide perovskites provided herein as a yellow phosphor, and the yellow phosphor is mixed with a blue phosphor. In a particular embodiment, the yellow phosphor is mixed with europium-doped barium magnesium aluminates ($BaMgAl_{10}O_{17}:Eu^{2+}$), which is a commercial blue phosphor. In a further embodiment, the devices provided herein are white light emitting devices.

In embodiments, the light emitting diodes comprise an anode, a cathode, and a light emitting layer. The light emitting diodes also may include at least one of an electron transport layer and a hole transport layer. The anode may comprise indium tin oxide (ITO). The cathode may comprise LiF/Al. In particular embodiments, the light emitting diodes may further comprise at least one of a hole injection layer, an electron injection layer, a hole blocking layer, and an electron blocking layer. In one embodiment, the light emitting layer comprises at least one of the metal halide perovskites of formula (I).

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

The following materials were used in the Examples: tin (II) bromide, N, N'-dimethylethylenediamine (99%) (Sigma-Aldrich); hydrobromic acid (48 wt. % in $H_2O$) (Sigma-Aldrich); dichloromethane (DCM, 99.9%) (VWR), dimethylformamide (DMF, 99.8%) (VWR), toluene (anhydrous, 99.8%) (VWR), and ethyl ether (VWR). All reagents and solvents were used without further purification unless otherwise stated.

Example 1—Solution Growth of $(C_4N_2H_{14})_4SnBr_{10}$ Bulk Crystals

N,N'-dimethylethylene-1,2-diammonium bromide salts were prepared by adding hydrobromic acid solution (2.2 equiv, 48%) into N, N'-dimethylethylenediamine (1 equiv) in ethanol at 0° C.

The organic salts were obtained after removal of the solvents and starting reagents under vacuum, followed by washing with ethyl ether. The salts were dried and kept in a desiccator for future use.

Tin(II) bromide and N, N'-dimethylethylene-1,2-diammonium bromide were mixed at 1:4 molar ratio and dissolved in DMF to form a clear precursor solution. Bulk single crystals were prepared by diffusing DCM into DMF solution at room temperature for overnight. The large colorless crystals were washed with acetone and dried under reduced pressure. The yield was calculated at ~70%.

Example 2—One Pot Synthesis of $(C_4N_2H_{14})_4SnBr_{10}$ Microsize Crystals Tin(II) bromide and N, N'-dimethylethylene-1,2-diammonium bromide were mixed at 1:4 molar ratio and dissolved in DMF to form a clear precursor solution.

Microsize perovskite crystals were precipitated by adding 1 mL of the solution to 5 mL toluene with vigorously stirring in a nitrogen filled glove box at room temperature.

The product was extracted from the crude solution via centrifugation and washed with toluene, affording a white powder in a yield of ~80% after dried under vacuum.

Example 3—Single Crystal X-Ray Diffraction (SCXRD)

The crystal structure of the bulk crystals was determined using single crystal X-Ray Diffraction (SCXRD). The SCXRD data is provided at Tables 1-3 below. The data showed a 0D structure with individual tin bromide octahedral $SnBr_6^{4-}$ ions completely isolated from each other and surrounded by $C_4N_2H_{14}^{2+}$ and Br ions, as depicted at FIG. 1A. It was believed that this unique 0D structure was a bulk assembly of core-shell quantum dots (see Yoffe, A. D., *Advances in Physics* 50, 1-208 (2001)), in which the organic shells wrapped around the core Sn bromide dots, as shown at FIG. 1B.

Table 1|Single crystal x-ray diffraction data and collection parameters. The collection was performed at a temperature of 120 K.

TABLE 1

Single crystal x-ray diffraction data and collection parameters. The collection was performed at a temperature of 120 K.

| Compound | $(C_4N_2H_{14})_4SnBr_{10}$ |
|---|---|
| Formula | $[(CH_3NH_2)_2C_2H_4]_4SnBr_{10}$ |
| Molecular weight | 1278.40 g/mol |
| Space group | P-1 (#2) |
| a | 10.2070(4) Å |
| b | 10.6944(4) Å |
| c | 18.5996(6) Å |
| α | 94.043(3) ° |
| β | 102.847(3)° |

TABLE 1-continued

Single crystal x-ray diffraction data and collection parameters. The collection was performed at a temperature of 120 K.

| Compound | $(C_4N_2H_{14})_4SnBr_{10}$ |
|---|---|
| γ | 97.904(3)° |
| V | 1949.89(12) Å$^3$ |
| Z | 2 |
| $\rho_{calc.}$ | 2.177 g/cm$^3$ |
| μ | 10.922 mm$^{-1}$ |
| Data collection range | 2.815° < θ < 34.220° |
| Reflections collected | 57392 |
| Independent reflections | 11532 |
| Parameters refined | 540 |
| Restraints | 240 |
| $R_1$, $wR_2$ | 0.0651$^a$, 0.0511$^b$ |
| Goodness-of-fit on $F^2$ | 0.9933 |

$^a R_1 = \Sigma ||F_o| - |F_c||/\Sigma |F_o|$.
$^b wR_2 = [\Sigma w(F_o^2 - F_c^2)^2/\Sigma w(F_o^2)^2]^{1/2}$ Table 2|Atomic positions of $(C_4N_2H_{14})_4SnBr_{10}$. All non-hydrogens were refined with anisotropic displacement parameters, while the hydrogens were refined with isotropic displacement parameters. All sites have Wyckoff position 2i.

TABLE 2

Atomic positions of $(C_4N_2H_{14})_4SnBr_{10}$. All non-hydrogens were refined with anisotropic displacement parameters, while the hydrogens were refined with isotropic displacement parameters. All sites have Wyckoff position 2i.

| Atom | x | y | z | $U_{eq}$, $U_{iso}$ (Å$^2$) |
|---|---|---|---|---|
| Sn1 | 0.50513(4) | 0.73268(3) | 0.25379(2) | 0.0165(2) |
| Br1 | 0.63291(5) | 0.68065(5) | 0.39545(3) | 0.0213(3) |
| Br2 | 0.36628(5) | 0.47903(5) | 0.22695(3) | 0.0201(2) |
| Br3 | 0.71126(5) | 0.65033(5) | 0.18028(3) | 0.0189(2) |
| Br4 | 0.28362(5) | 0.82142(5) | 0.32885(3) | 0.0209(3) |
| Br5 | 0.65333(6) | 1.02790(5) | 0.28467(3) | 0.0259(3) |
| Br6 | 0.35651(6) | 0.77645(5) | 0.08009(3) | 0.0238(3) |
| Br7 | 0.89569(6) | 1.31403(5) | 0.15163(3) | 0.0199(3) |
| Br8 | 0.89768(6) | 1.30727(5) | 0.48454(3) | 0.0208(3) |
| Br9 | −0.12538(6) | 0.79197(5) | −0.02452(3) | 0.0216(3) |
| Br10 | 0.14702(6) | 0.16762(5) | 0.35492(3) | 0.0264(3) |
| N1 | −0.1487(4) | 0.3684(4) | 0.3152(2) | 0.0185(2) |
| N2 | 0.1579(4) | 0.4614(4) | 0.4116(2) | 0.0173(2) |
| N3 | 0.8478(4) | 1.0173(4) | 0.0913(2) | 0.0186(2) |
| N4 | 1.1552(4) | 1.1009(4) | 0.1836(2) | 0.0202(2) |
| N5 | 0.4943(5) | 1.0797(4) | 0.4118(2) | 0.0258(3) |
| N6 | 0.5755(4) | 0.3819(4) | 0.0600(2) | 0.0193(2) |
| N7 | 1.0250(4) | 0.9133(4) | 0.4135(2) | 0.0201(2) |
| N8 | 0.1107(4) | 0.5285(4) | 0.0968(2) | 0.0197(2) |
| C9 | −0.0652(5) | 0.4954(5) | 0.3320(3) | 0.0182(3) |
| C10 | 0.0849(5) | 0.4963(5) | 0.3395(3) | 0.0212(3) |
| C11 | 0.3103(5) | 0.4950(5) | 0.4238(3) | 0.0230(3) |
| C12 | −0.2975(5) | 0.3758(5) | 0.3025(3) | 0.0207(3) |
| C13 | 0.9227(5) | 0.9734(5) | 0.1602(3) | 0.0203(3) |
| C14 | 1.0719(6) | 0.9736(5) | 0.1650(3) | 0.0220(3) |
| C15 | 1.3043(6) | 1.0942(5) | 0.1964(3) | 0.0246(3) |
| C16 | 0.6981(6) | 0.9905(5) | 0.0830(3) | 0.0268(3) |
| C17 | 0.5067(6) | 1.2206(6) | 0.4308(3) | 0.0305(3) |
| C18 | 0.5471(6) | 1.0070(5) | 0.4745(3) | 0.0263(3) |
| C19 | 0.4689(5) | 0.4533(5) | 0.0221(3) | 0.0207(3) |
| C20 | 0.5201(6) | 0.2788(5) | 0.1004(3) | 0.0249(3) |
| C21 | 0.9498(5) | 0.9674(5) | 0.4659(3) | 0.0189(3) |
| C22 | 0.9346(5) | 0.8435(5) | 0.3441(3) | 0.0206(3) |
| C23 | 0.0734(5) | 0.5268(5) | 0.0151(3) | 0.0167(3) |
| C24 | 0.0588(6) | 0.6265(5) | 0.1381(3) | 0.0228(3) |
| H11 | −0.126(2) | 0.325(2) | 0.3526(13) | 0.028(2) |
| H12 | −0.133(2) | 0.327(2) | 0.2764(13) | 0.027(2) |
| H21 | 0.129(2) | 0.498(3) | 0.4479(12) | 0.026(2) |
| H22 | 0.139(2) | 0.3787(19) | 0.4125(15) | 0.026(2) |
| H31 | 0.873(2) | 1.0995(19) | 0.0918(15) | 0.029(2) |
| H32 | 0.870(2) | 0.980(3) | 0.0524(12) | 0.029(2) |
| H41 | 1.131(2) | 1.145(2) | 0.1472(13) | 0.031(2) |
| H42 | 1.138(2) | 1.140(2) | 0.2225(13) | 0.031(2) |
| H51 | 0.541(3) | 1.068(2) | 0.3776(14) | 0.039(2) |
| H52 | 0.410(2) | 1.046(2) | 0.3915(16) | 0.039(2) |

TABLE 2-continued

Atomic positions of $(C_4N_2H_{14})_4SnBr_{10}$. All non-hydrogens were refined with anisotropic displacement parameters, while the hydrogens were refined with isotropic displacement parameters. All sites have Wyckoff position 2i.

| Atom | x | y | z | $U_{eq}$, $U_{iso}$ (Å²) |
|---|---|---|---|---|
| H61 | 0.642(2) | 0.434(2) | 0.0903(13) | 0.028(2) |
| H62 | 0.619(3) | 0.350(2) | 0.0275(13) | 0.028(2) |
| H71 | 1.083(3) | 0.976(2) | 0.4017(14) | 0.030(2) |
| H72 | 1.075(3) | 0.861(2) | 0.4371(12) | 0.030(2) |
| H81 | 0.200(2) | 0.533(3) | 0.1126(13) | 0.029(2) |
| H82 | 0.080(3) | 0.452(2) | 0.1078(13) | 0.028(2) |
| H91 | −0.081(3) | 0.532(3) | 0.3771(13) | 0.022(2) |
| H92 | −0.097(2) | 0.542(2) | 0.2916(14) | 0.022(2) |
| H101 | 0.124(2) | 0.580(2) | 0.3343(16) | 0.025(2) |
| H102 | 0.096(3) | 0.435(3) | 0.3013(13) | 0.026(2) |
| H111 | 0.357(3) | 0.463(4) | 0.4678(16) | 0.036(2) |
| H112 | 0.337(3) | 0.587(2) | 0.429(2) | 0.035(2) |
| H113 | 0.337(3) | 0.458(4) | 0.3828(16) | 0.035(2) |
| H123 | −0.350(3) | 0.293(2) | 0.288(2) | 0.031(2) |
| H122 | −0.318(3) | 0.412(4) | 0.3468(14) | 0.031(2) |
| H121 | −0.323(3) | 0.427(3) | 0.2635(17) | 0.031(2) |
| H131 | 0.913(3) | 1.029(3) | 0.2012(12) | 0.025(2) |
| H132 | 0.883(2) | 0.888(2) | 0.1617(16) | 0.025(2) |
| H141 | 1.105(3) | 0.924(2) | 0.2044(14) | 0.026(2) |
| H142 | 1.087(3) | 0.940(3) | 0.1188(13) | 0.026(2) |
| H151 | 1.355(3) | 1.178(2) | 0.211(2) | 0.037(2) |
| H152 | 1.322(3) | 1.058(4) | 0.1514(14) | 0.037(2) |
| H153 | 1.328(3) | 1.042(3) | 0.2353(18) | 0.037(2) |
| H163 | 0.651(3) | 1.023(4) | 0.0395(16) | 0.039(2) |
| H162 | 0.675(3) | 1.031(4) | 0.1248(16) | 0.039(2) |
| H161 | 0.666(3) | 0.900(2) | 0.079(2) | 0.039(2) |
| H173 | 0.463(4) | 1.257(3) | 0.3877(14) | 0.044(2) |
| H172 | 0.601(2) | 1.255(3) | 0.446(2) | 0.045(2) |
| H171 | 0.462(4) | 1.237(3) | 0.4705(19) | 0.045(2) |
| H181 | 0.634(2) | 1.052(3) | 0.5003(13) | 0.030(2) |
| H182 | 0.560(3) | 0.925(2) | 0.4537(14) | 0.030(2) |
| H191 | 0.436(3) | 0.500(2) | 0.0596(13) | 0.025(2) |
| H192 | 0.397(2) | 0.395(2) | −0.0089(14) | 0.025(2) |
| H203 | 0.591(3) | 0.234(3) | 0.123(2) | 0.035(2) |
| H202 | 0.479(4) | 0.313(3) | 0.1381(18) | 0.036(2) |
| H201 | 0.453(3) | 0.220(3) | 0.0662(14) | 0.036(2) |
| H211 | 0.901(3) | 1.028(2) | 0.4411(13) | 0.024(2) |
| H212 | 0.892(3) | 0.899(2) | 0.4794(14) | 0.024(2) |
| H223 | 0.988(3) | 0.804(3) | 0.3149(16) | 0.029(2) |
| H222 | 0.888(3) | 0.903(2) | 0.3172(16) | 0.029(2) |
| H221 | 0.868(3) | 0.782(3) | 0.3574(15) | 0.029(2) |
| H231 | 0.089(3) | 0.613(2) | 0.0028(14) | 0.020(2) |
| H232 | 0.126(2) | 0.475(3) | −0.0067(13) | 0.021(2) |
| H243 | 0.108(3) | 0.636(3) | 0.1880(12) | 0.035(2) |
| H242 | 0.073(4) | 0.704(2) | 0.1169(18) | 0.035(2) |
| H241 | −0.036(2) | 0.600(3) | 0.135(2) | 0.035(2) |

Table 3|Selected bonds and angles for $(C_4N_2H_{14})_4SnBr_{10}$.

TABLE 3

Selected bonds and angels for

| Bond | Distance (Å) |
|---|---|
| Sn1—Br1 | 2.798 |
| Sn1—Br2 | 2.838 |
| Sn1—Br3 | 2.948 |
| Sn1—Br4 | 3.125 |
| Sn1—Br5 | 3.260 |
| Sn1—Br6 | 3.345 |
| Br1—Br8 | 4.795 |
| Br1—Br10 | 4.747 |
| Br2—Br7 | 4.741 |
| Br2—Br9 | 4.583 |
| Br2—Br10 | 4.817 |
| Br3—Br7 | 4.336 |
| Br3—Br9 | 4.746 |
| Br4—Br8 | 4.494 |
| Br4—Br10 | 4.166 |
| Br5—Br7 | 4.828 |
| Br5—Br8 | 4.607 |

TABLE 3-continued

Selected bonds and angels for

| | |
|---|---|
| Br5—Br10 | 4.905 |
| Br6—Br7 | 4.464 |
| Br6—Br9 | 4.901 |
| Br7—Br9 | 3.897 |
| Br8—Br10 | 4.217 |

| Bonds | Angle (°) |
|---|---|
| Br1—Sn1—Br6 | 176.22 |
| Br2—Sn1—Br5 | 177.75 |
| Br3—Sn1—Br4 | 178.91 |

The foregoing single crystal x-ray diffraction data of $(C_4N_2H_{14})_4SnBr_{10}$ was collected using an Oxford-Diffraction Xcalibur-2 CCD diffractometer with graphite-monochromated Mo Kα radiation.

The crystal was mounted in a cryoloop under Paratone-N oil and cooled to 120 K with an Oxford-Diffraction Cryojet. A complete sphere of data was collected using ω scans with 1° frame widths to a resolution of 0.6 Å, equivalent to 2θ≈72.5°.

Reflections were recorded, indexed and corrected for absorption using the Oxford-Diffraction CrysAlisPro software, and subsequent structure determination and refinement was carried out using CRYSTALS, employing Superflip to solve the crystal structure. The data did not allow for an unconstrained refinement: all hydrogens were restrained to the connecting nitrogen or carbon.

The refinement was performed against $F^2$, with anisotropic thermal displacement parameters for all non-hydrogen atoms and with isotropic thermal displacement parameters for the hydrogens in the structure. Diamond was used as the crystal structure visualization software for the images presented in the manuscript.

Example 4—Powder X-Ray Diffraction (PXRD)

The PXRD analysis was performed on Panalytical X'PERT Pro Powder X-Ray Diffractometer using Copper X-ray tube (standard) radiation at a voltage of 40 kV and 40 mA, and X'Celerator RTMS detector. The diffraction pattern was scanned over the angular range of 5-50 degree (2θ) with a step size of 0.02, at room temperature. Simulated powder patterns were calculated by Mercury software using the crystallographic information file (CIF) from single-crystal x-ray experiment.

Figure 2:
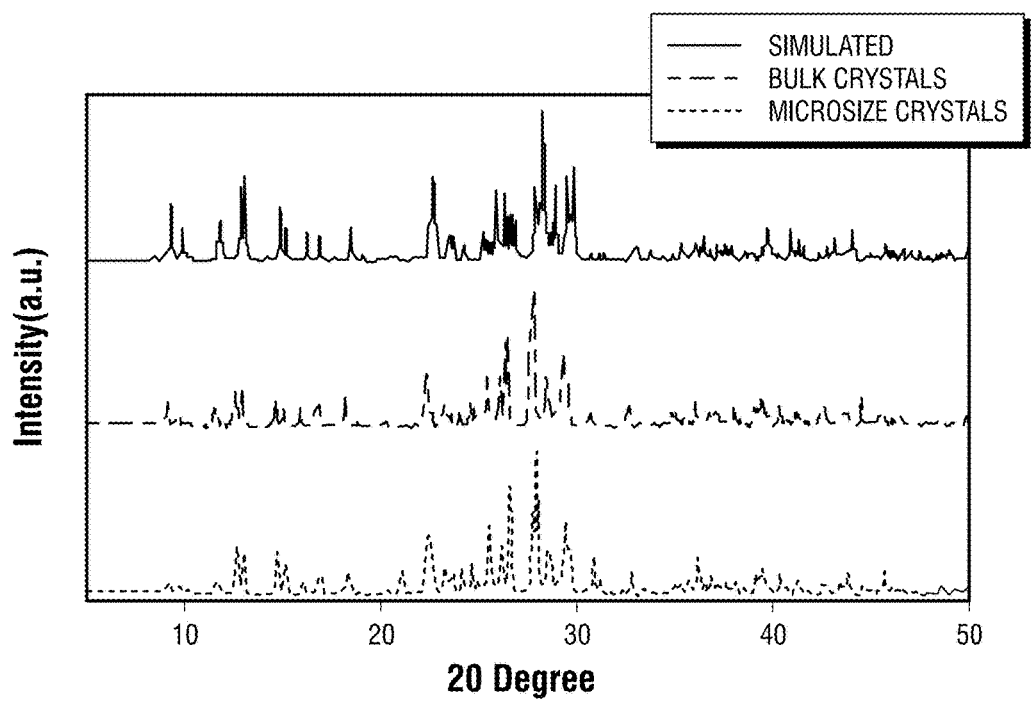
FIG. 2 is a depiction of the powder X-ray diffraction patterns of one embodiment of a metal halide perovskite in bulk crystal form and micro crystal form.

The powder XRD (PXRD) patterns of ball-milled powders of bulk crystals (Example 1) and microsize crystals (Example 2) displayed almost identical features, as shown at FIG. 2, which was believed to indicate that both samples had the same crystal structure.

Example 5—Thermogravimetry Analysis (TGA), Atomic Force Microscopy (AFM), and Scanning Electron Microscopy (SEM)

Figure 3:
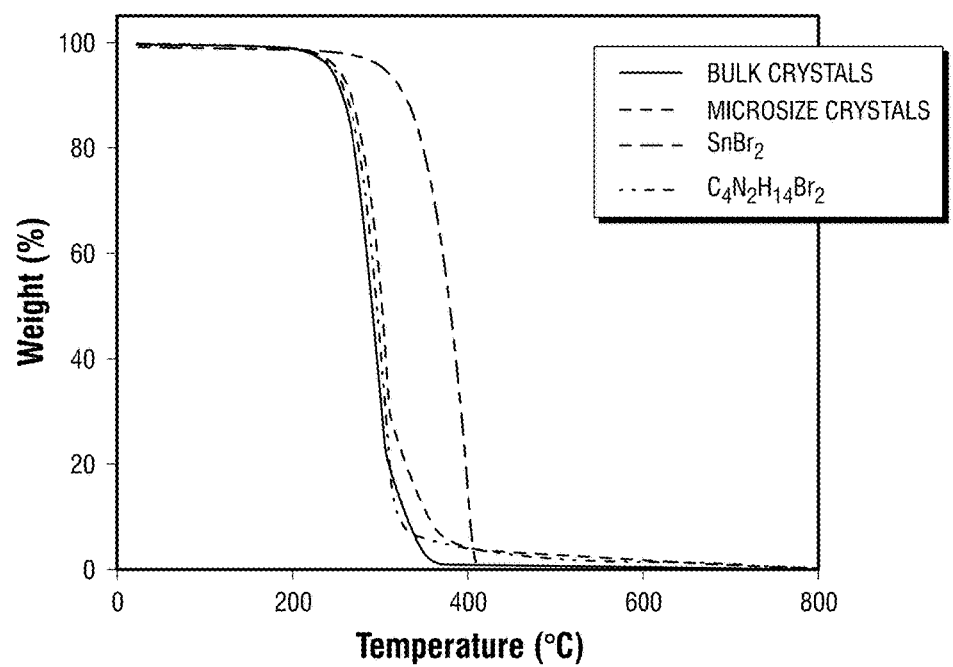
FIG. 3 is a plot of thermogravimetric analysis data collected for one embodiment of a metal halide perovskite in bulk crystal form and micro crystal form, and for $SnBr_2$ and $C_4N_2H_{14}Br_2$.

Thermogravimetric Analysis (TGA)(FIG. 3), Atomic Force Microscopy (AFM)(FIG. 4A, FIG. 4B, and FIG. 4C), and Scanning Electron Microscopy (SEM)(FIG. 5) were also used to characterize the prepared samples, which further confirmed that the bulk crystals prepared by solution growth and the microsize crystals prepared by one-pot synthesis possess the same compositions with only difference in crystal size.

TGA was carried out using a TA instruments Q50 TGA system. The samples were heated from room temperature (~22° C.) to 800° C. with at a rate of 5° C.·min$^{-1}$, under an argon flux of 40 mL·min$^{-1}$.

Figure 4A:
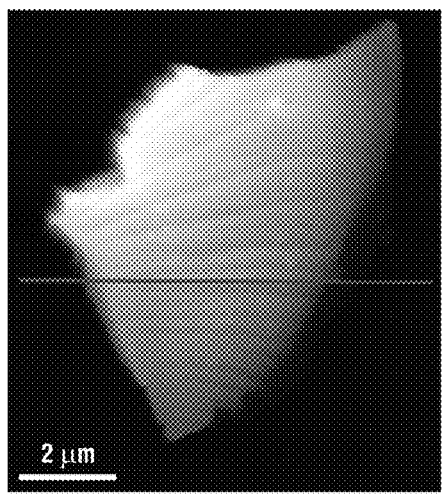
FIG. 4A is a 2D AFM image of one embodiment of a microsize crystal.
Figure 4B:
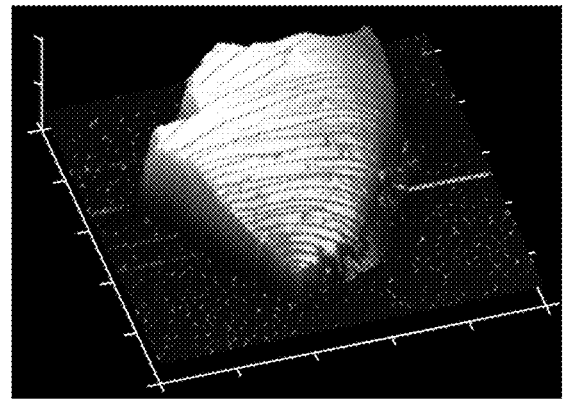
FIG. 4B is a 3D AFM image of the microsize crystal of FIG. 4A.
Figure 4C:
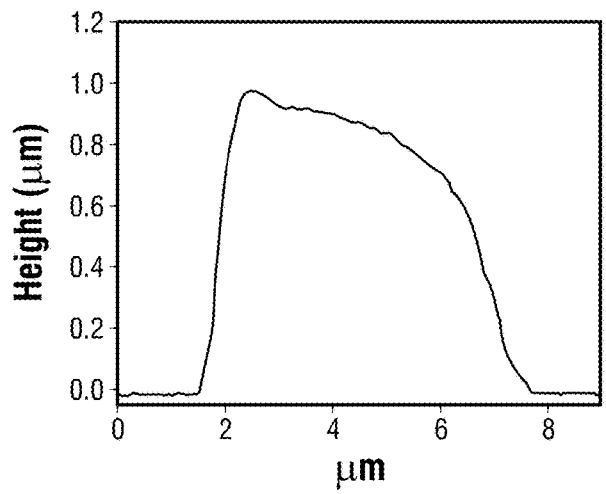
FIG. 4C is a height profile of the 2D AFM image of FIG. 4A.
Figure 5A:
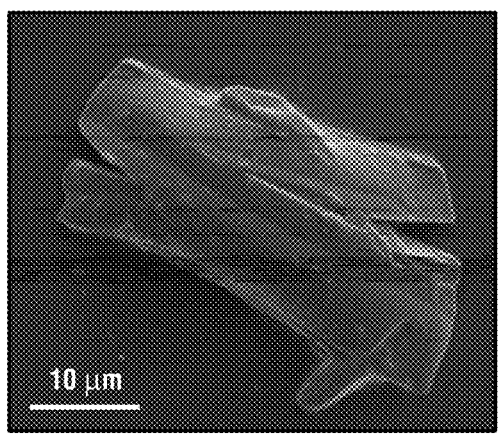
FIG. 5A is an SEM image of one embodiment of a micro size metal halide perovskite crystal.
Figure 5B:
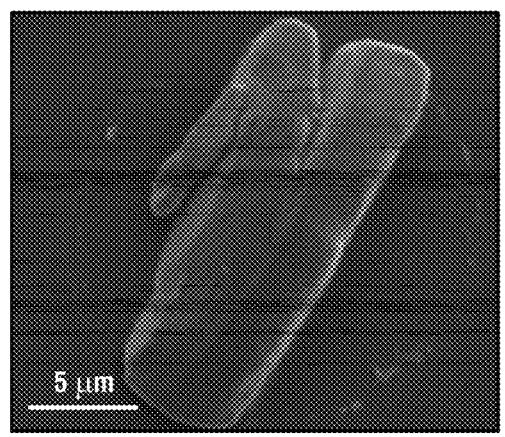
FIG. 5B is an SEM image of one embodiment of a micro size metal halide perovskite crystal.
Figure 5C:
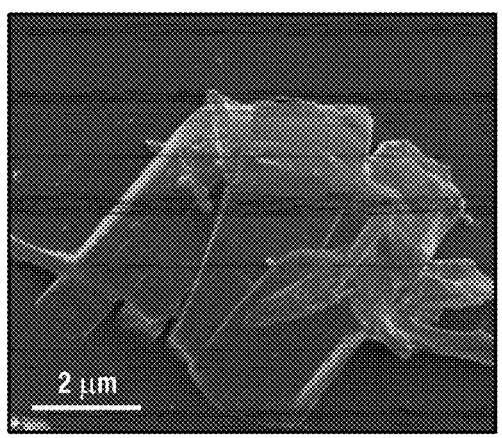
FIG. 5C is an SEM image of one embodiment of a micro size metal halide perovskite crystal.
Figure 5D:
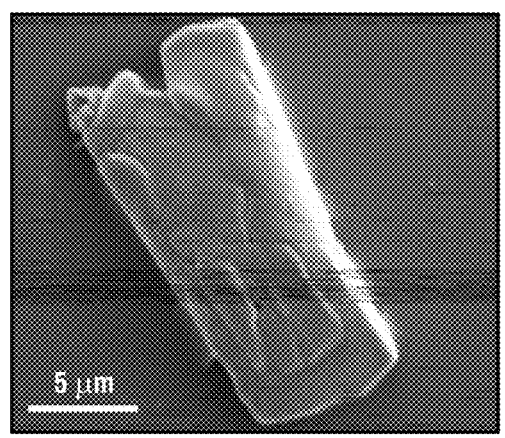
FIG. 5D is an SEM image of one embodiment of a micro size metal halide perovskite crystal.

AFM measurements were conducted using Bruker Icon. All measurements were performed in the standard tapping mode in air with OTESPA tips from Bruker. FIG. 4A is a 2D AFM image of a microsize crystal (Example 2), and FIG. 4B is a 3D AFM image of the same crystal. FIG. 4C is a height profile of the 2D AFM image of FIG. 4A.

SEM images were taken using a FEI Nova NanoSEM 400. FIG. 5A, FIG. 5B, FIG. 5C, and FIG. 5D are SEM images of the 0D Sn bromide perovskite of Example 2.

Example 6—Absorption Spectrum Measurements and Photoluminescence Steady State Studies Absorption spectra of both the bulk (Example 1) and microsize (Example 2) perovskite crystals were measured at room temperature through synchronous scan in an integrating sphere incorporated into the spectrofluorometer (FLS980, Edinburgh Instruments) while maintaining a 1 nm interval between the excitation and emission monochromators.

Steady-state photoluminescence spectra of both bulk (Example 1) and microsize (Example 2) crystals in solid state were obtained at room temperature and 77 K (liquid nitrogen was used to cool the samples) on a FLS980 spectrofluorometer.

Figure 6:
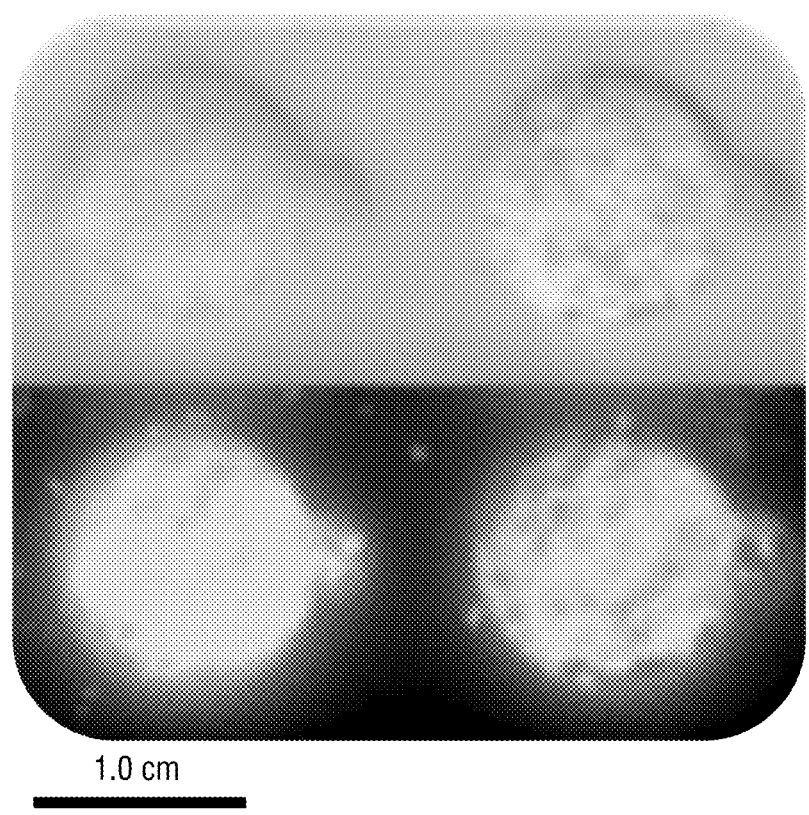
FIG. 6 includes images of bulk and microsize crystals of one embodiment of a metal halide perovskite under ambient light and UV light.

The photophysical properties of the prepared bulk and microsize 0D Sn bromide perovskite crystals were investigated using UV-Vis absorption spectroscopy, as well as steady state and time-resolved photoluminescence spectroscopies. FIG. 6 depicts the images of the bulk and microsize crystals under ambient light and a hand-held UV lamp irradiation (365 nm). Both the bulk and microsize crystals showed white color under ambient light, and displayed strong yellow emission under UV irradiation.

Figure 7:
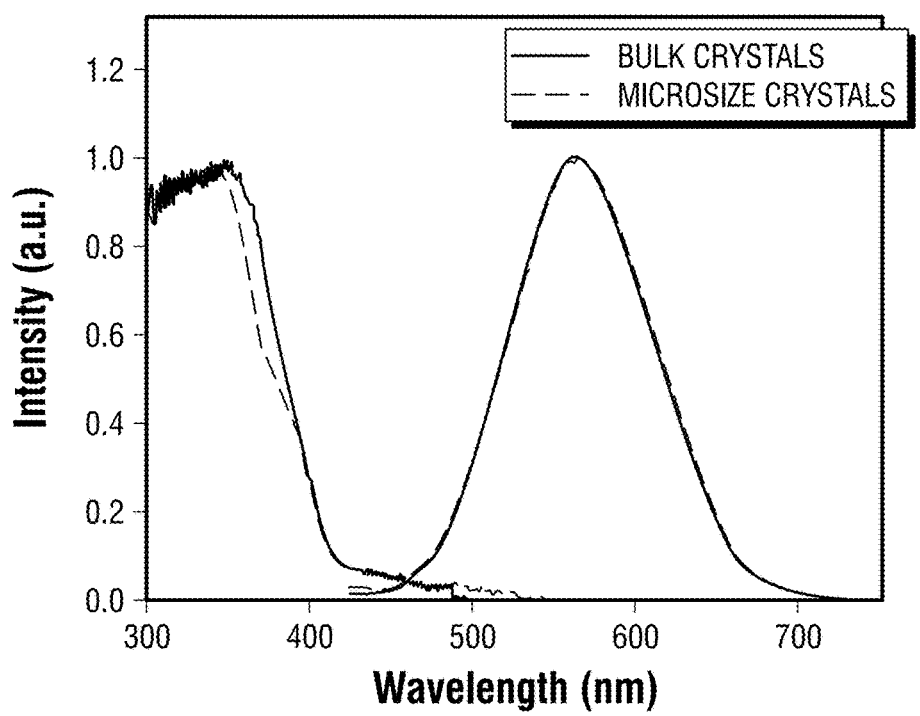
FIG. 7 depicts absorption and emission spectra of one embodiment of a metal halide perovskite in bulk crystal and micro crystal form.

FIG. 7 depicts the absorption and emission spectra of the bulk (Example 1) and microsize (Example 2) crystals.

A large apparent Stokes shift of >0.7 eV between the absorption and emission is observed, with the absorption edged at around 425 nm and the emission peaked at around 570 nm. The yellow emission also displayed a large full width at half maximum (FWHM) of ~105 nm (0.40 eV), which is similar to that of the widely used cerium-doped yttrium aluminum garnet (Ce:YAG) yellow phosphor (see Tucureanu, V., et al. *Opto-Electron Rev* 23, 239-251, (2015)).

The broadband yellow emission with large apparent Stokes shift was believed to suggest that it was not from the direct free exciton excited states, but rather other excited states with lower energy. It is known for metal halides that the formation of self-trapped excited states can be dependent on the dimensionality of the crystalline systems (see, e.g., Williams, R. T. et al. *Journal of Physics and Chemistry of Solids* 51, 679-716 (1990); Shinozuka, Y. et al. *Journal of the Physical Society of Japan* 64, 3007-3017(1995); Georgiev, M., et al. *Pure Appl Chem* 67, 447-456 (1995); Ishida, K. *Z Phys B Con Mat* 102, 483-491(1997); and Wu, X. X. et al. *J Am Chem Soc* 137, 2089-2096 (2015)).

It was believed that 0D structured systems with the strongest quantum confinement would be most favorable for the formation of self-trapped excited states, because, at least in part, there was no potential energy barrier separating the free exciton and self-trapped excited states. The yellow emission from the 0D Sn bromide perovskites was very similar to the 2.2 eV emission from SnBr$_2$ crystals at low temperature, which was believed to be attributed to the radiative decay of self-trapped excitons (see Yamasaki, Y. et al. *International Journal of Modern Physics B* 15, 4009-4012 (2001)).

Figure 8:
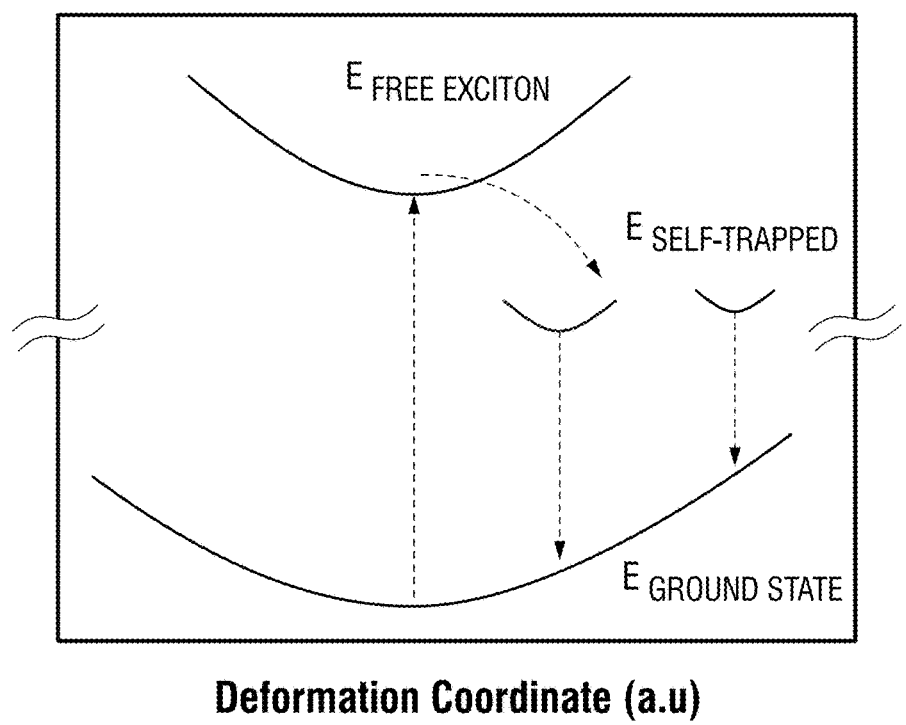
FIG. 8 depicts the mechanism of exciton self-trapping of one embodiment of a metal halide perovskite.

Therefore, the excited state processes for the 0D Sn bromide perovskites of the foregoing examples could be depicted in the configuration coordinate diagram shown at FIG. 8. FIG. 8 depicts the mechanism of exciton self-trapping, including a configuration coordinate diagram for the self-trapped excitons in 0D Sn bromide perovskites (the straight and curved arrows represent optical and relaxation situations, respectively). Upon photon absorption, the perovskites were excited to the high energy free exciton excited states, which were believed to undergo ultrafast relaxation to the lower energy multiple self-trapped excited states to generate broadband photoluminescence. This behavior appeared to be very similar to that of heavy metal phosphorescent materials, because the molecules were believed to be photo-excited to the singlet states, which underwent ultrafast intersystem crossing to form the lower energy triplet states that caused phosphorescent emission. Unlike corrugated 2D and 1D perovskites emitting from both free exciton and self-trapped excited states at room temperature due to thermally activated equilibrium, the 0D perovskites of the foregoing examples were believed to emit from the self-trapped excited states only, further confirming that 0D structures most favor exciton self-trapping.

Example 7—Photoluminescence Quantum Efficiencies (PLQEs)

Figure 9:
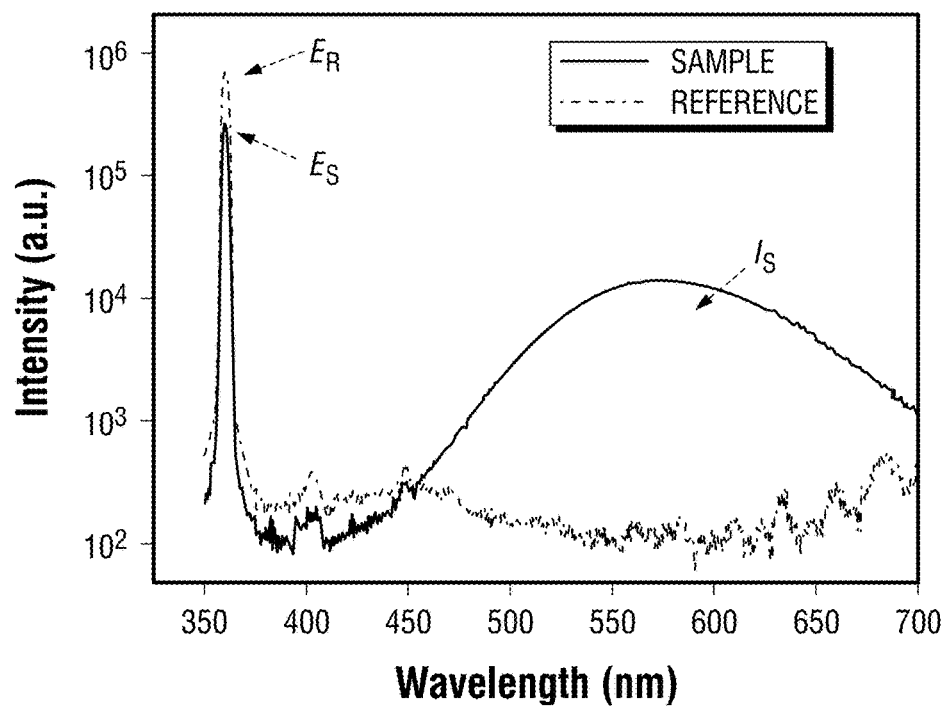
FIG. 9 depicts the spectra for a PLQE measurement of one embodiment of a metal halide perovskite.

The PLQEs of bulk (Example 1) and microsize (Example 2) crystals were measured to be near-unity (95±5%), as shown at FIG. 9, which was believed to be the highest value yet achieved for any metal halide perovskite. FIG. 9 shows the excitation line of reference and emission spectrum of the metal halide perovskite of Example 1 collected by an integrated sphere.

For photoluminescence quantum efficiency measurement, the samples were excited using light output from a housed 450 W Xe lamp passed through a single grating (1800 l/mm, 250 nm blaze) Czerny-Turner monochromator and finally a 5 nm bandwidth slit.

Emission from the sample was passed through a single grating (1800 l/mm, 500 nm blaze) Czerny-Turner monochromator (5 nm bandwidth) and detected by a Peltier-cooled Hamamatsu R928 photomultiplier tube. The absolute quantum efficiencies were acquired using an integrating sphere incorporated into the FLS980 spectrofluorometer.

The PLQE was calculated by the equation: $\eta_{QE}=I_S/(E_R-E_S)$, in which $I_S$ represents the luminescence emission spectrum of the sample, $E_R$ is the spectrum of the excitation light from the empty integrated sphere (without the sample), and $E_S$ is the excitation spectrum for exciting the sample.

Control samples, rhodamine 101 and blue phosphor BaMgAl$_{10}$O$_{17}$:Eu$^{2+}$, were measured using this method to give PLQEs of ~98% and ~93%, which are close to the literature reported values. The PLQEs were double confirmed by a Hamamatsu C9920 system equipped with a xenon lamp, calibrated integrating sphere and model C10027 photonic multi-channel analyzer (PMA).

Example 8—Time-Resolved Photoluminescence

Figure 10:
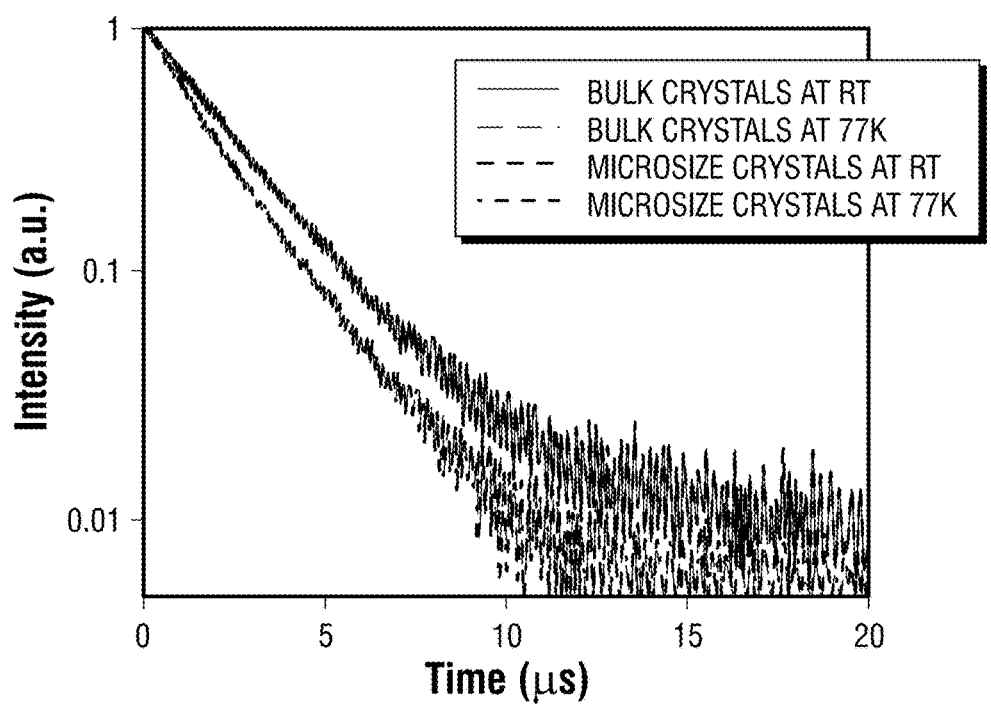
FIG. 10 depicts the emission decays at room temperature and 77 K of one embodiment of a metal halide perovskite having a bulk crystal size and micro crystal size.

FIG. 10 depicts the decay curves of yellow emissions from the bulk and microsize crystals at room temperature, giving almost identical lifetimes of ~2.2 μs.

Time-Resolved Emission data were collected at room temperature and 77 K (liquid nitrogen was used to cool the samples) using time-correlated single photon counting on a Horiba JY Fluoromax-4 Fluorometer. Samples were excited with 295 nm pulsed diode lasers. Emission counts were monitored at 530 nm. The average lifetime was obtained by multiexponential fitting.

Example 9—PL Intensity Dependence on Excitation Power Density

Figure 11:
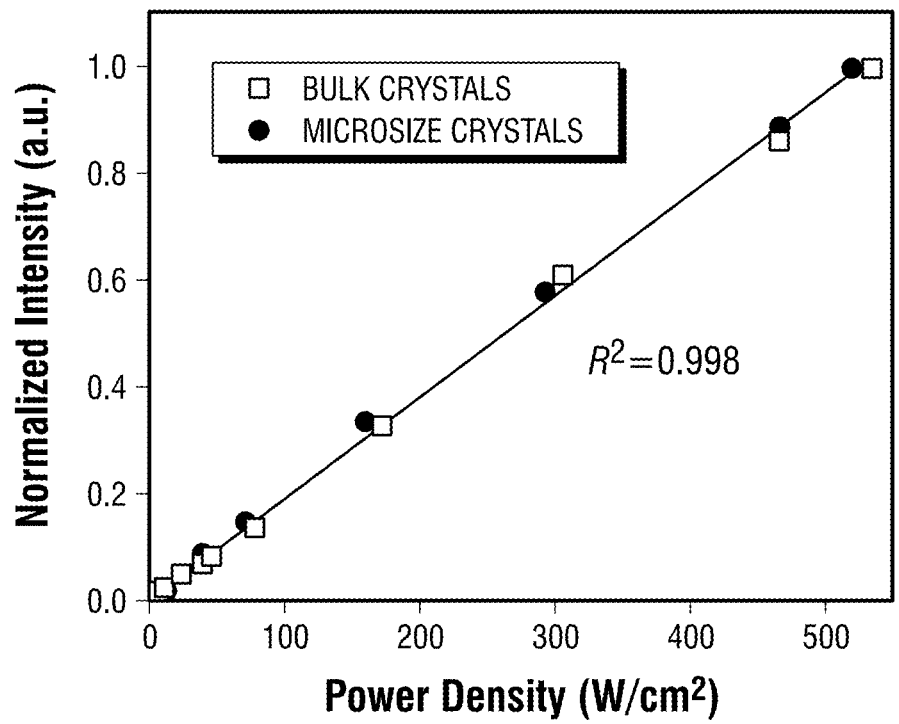
FIG. 11 depicts the emission intensity versus excitation power for bulk and micro crystals of one embodiment of a metal halide perovskite.

To verify the origin of the yellow emission from the intrinsic self-trapped excited states, the dependence of emission intensity on excitation power for bulk (Example 1) and microsize (Example 2) crystals at room temperature was measured, as well as their emissions at 77 K. As shown in FIG. 11, the intensity of the broadband emission exhibits a linear dependence on the excitation power up to 500 W/cm$^2$, which was believed to suggest that the emission did not arise from permanent defects (see Dohner, E. R., et al. *J Am Chem Soc* 136, 13154-13157 (2014)).

Figure 12:
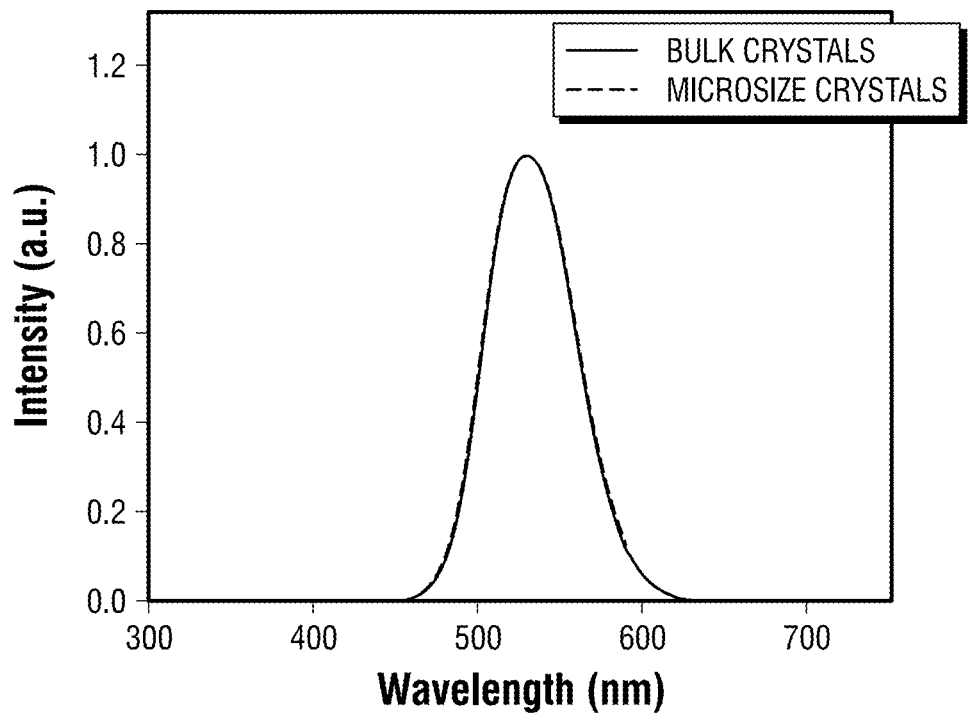
FIG. 12 depicts the emission spectra (excited at 360 nm) at 77 K of bulk and micro crystals of one embodiment of a metal halide perovskite.

FIG. 12 shows the emission spectra of bulk and microsize crystals at 77 K, which have a much smaller FWHM of 62 nm, as compared to 105 nm at room temperature. This narrowing was consistent with the theoretical and experimental results obtained for lead halide perovskites with exciton self-trapping, where there are multiple self-trapped excited states and vibrational bands giving different emission energies at room temperature, but fewer favorable ones with less vibrational transactions at low temperature.

The emission peaks blue shift at 77 K (from 570 to 530 nm) with the lifetimes (~2.0 µs) slightly shorter than those at room temperature, which was believed to suggest that the excitons may concentrate more on the lower energy excited states with larger band gap and faster decay rate, i.e. the first downward pointing arrow in FIG. 8.

PL intensity versus power studies were carried out on an Edinburgh Instruments PL980-KS transient absorption spectrometer using a Continuum Nd:YAG laser (Surelite EX) pumping a Continuum Optical Parametric Oscillator (Horizon II OPO) to provide 360 nm 5 ns pulses at 1 Hz. The pump beam profile was carefully defined by using collimated laser pulses passed through an iris set to 5 mm diameter. Pulse intensity was monitored by a power meter (Ophir PE10BF-C) detecting the reflection from a beam splitter. The power meter and neutral density filters were calibrated using an identical power meter placed at the sample position. Neutral density filters and an external power attenuator were used to reduce the pump's power density to the desired power range. Detection consisted of an Andor intensified CCD (1024×256 element) camera collecting a spectrum from 287 nm to 868 nm and gated to optimize PL collection (typically a 30 to 50 ns gate depending on PL lifetime starting immediately following the 5 ns laser pulse). 100 collections were averaged at each power level with every laser pulse monitored to determine the average intensity. PL intensity was determined at the maximum of the PL emission curve.

Example 10—Materials Photostability Study

To test the photostability, a 100 W 20 V mercury short arc lamp was used as continuous irradiation light source. The intensity of the irradiation was calibrated to 150 mW/cm$^2$. The photoluminescence was measured at periodic intervals on a HORIBA iHR320 spectrofluorimeter, equipped with a HORIBA Synapse CCD detection system.

Figure 13:
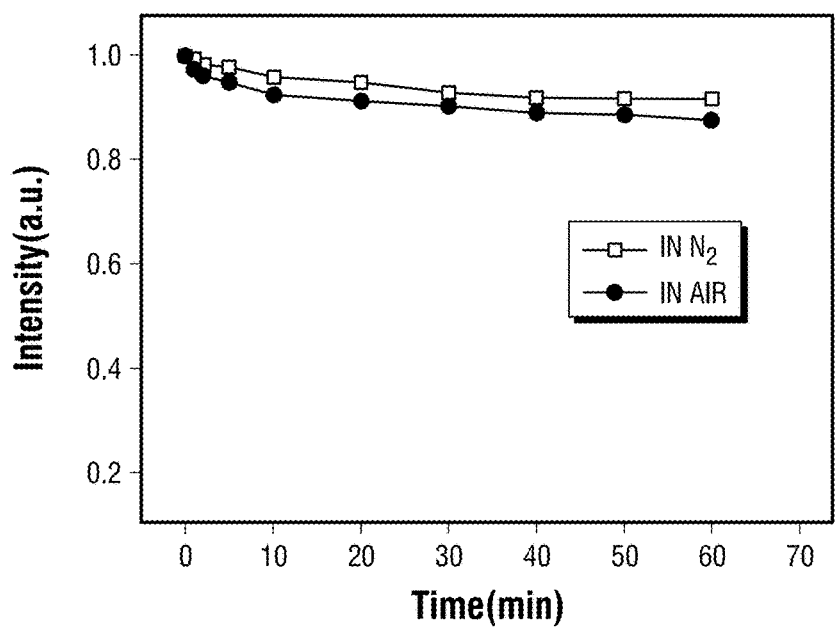
FIG. 13 depicts the photoluminescence stability of one embodiment of a metal halide perovskite under continuous illumination using a high power mercury lamp (150 mW/cm$^2$).

The Sn based materials of the foregoing examples showed great photostability under continuous high power mercury lamp irradiation (150 mW/cm$^2$), with more stable emission recorded in nitrogen environment than in air (FIG. 13).

Example 11—UV Pumped LEDs

To demonstrate the potential application of the foregoing 0D Sn bromide perovskites as yellow phosphor, optically pumped white LEDs were fabricated by blending the microsize crystals (Example 2) with commercial blue phosphors (BaMgAl$_{10}$O$_{17}$:Eu$^{2+}$) in a polydimethylsiloxane (PDMS) matrix.

Figure 14:
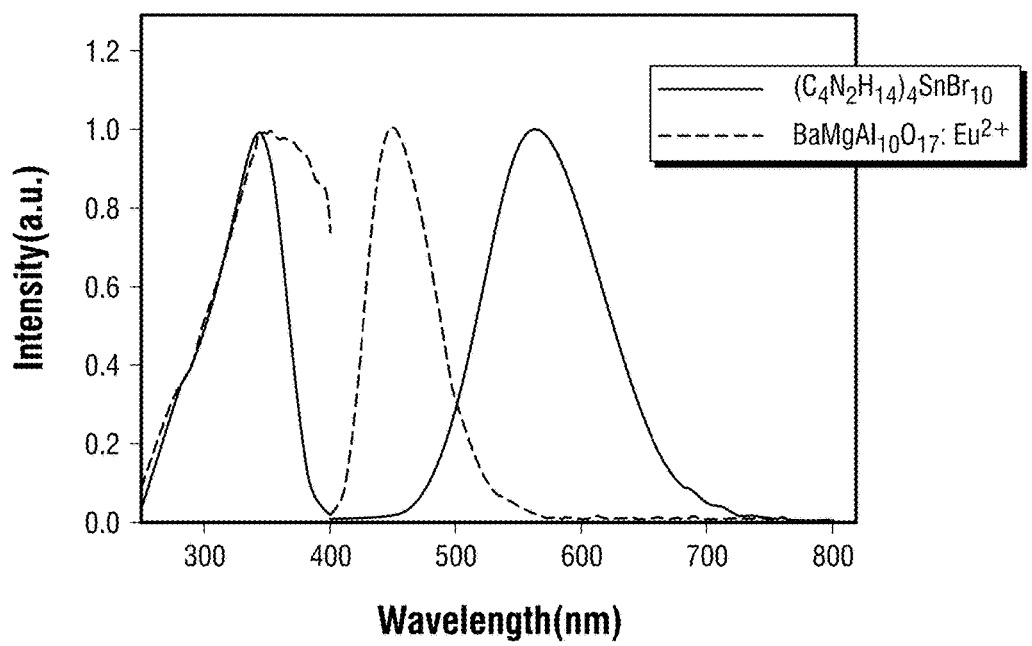
FIG. 14 depicts the normalized excitation and emission spectra of a commercial blue phosphor and one embodiment of a metal halide perovskite that is a yellow phosphor.
Figure 15:
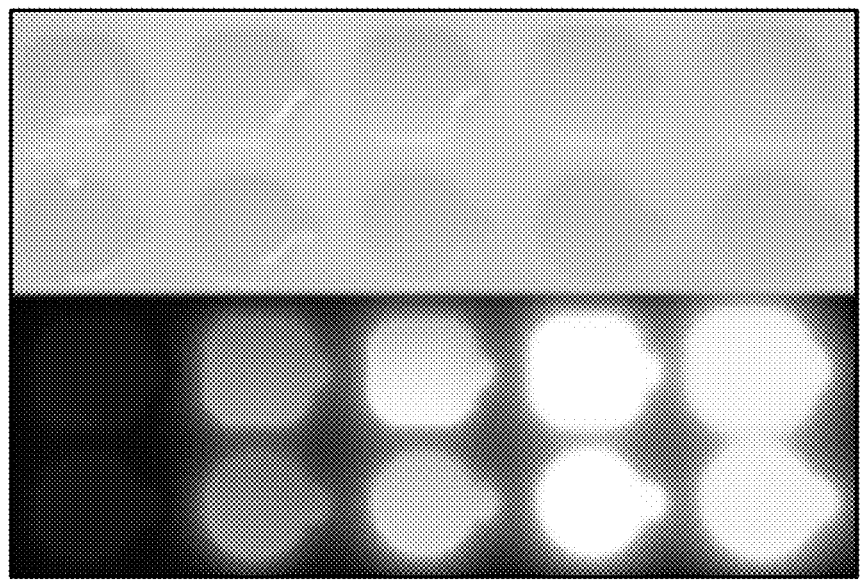
FIG. 15 includes images of different embodiments of blue and yellow phosphors, and their blends with different weight ratios.

Considering the excitations of both the yellow and blue phosphors in the UV region (see FIG. 14), a commercial UV LED (340 nm) was used as the light source. FIG. 15 depicts the images of blue phosphors, yellow phosphors, and their blends with different weight rations (1:2, 1:1, and 2:1) embedded in PDMS under ambient light and a hand-held UV lamp irradiation.

Figure 16:
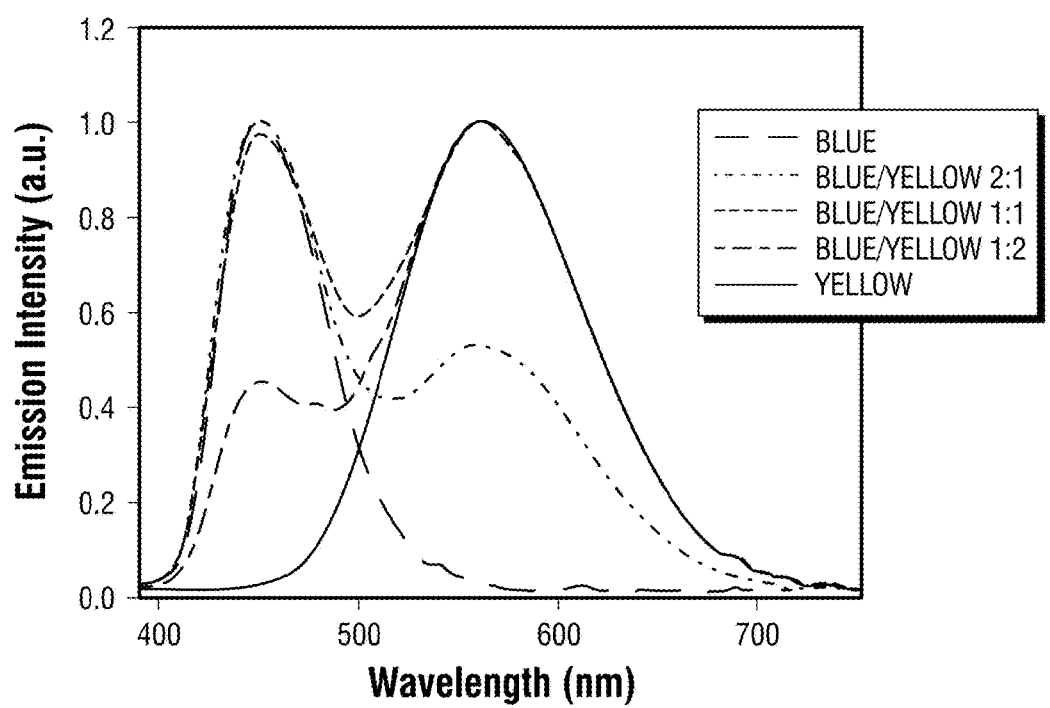
FIG. 16 depicts emission spectra of one embodiment of a UV pumped light emitting diode with different blending ratios of blue and yellow phosphors.
Figure 17:
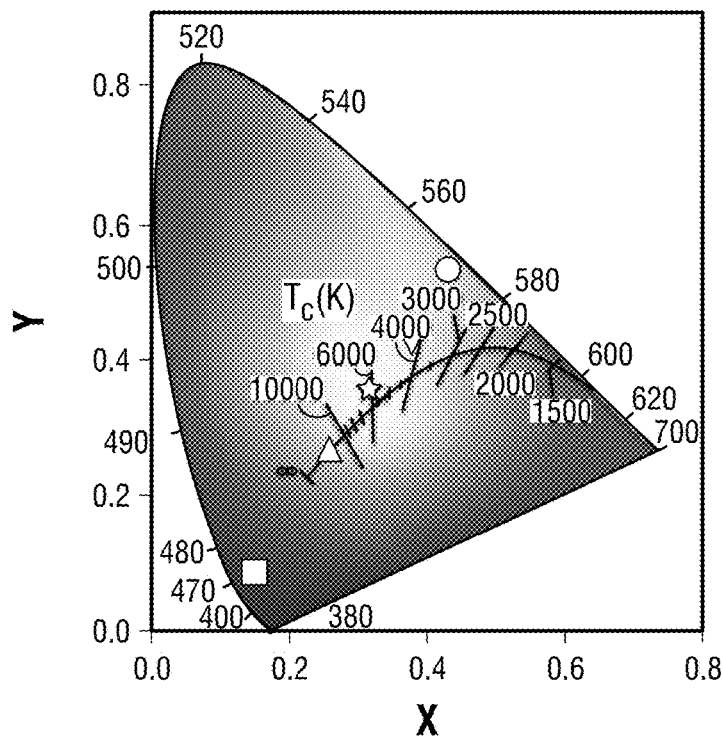
FIG. 17 depicts a chromaticity chart for one embodiment of a UV pumped light emitting diode with different blending ratios of blue and yellow phosphors.

The emission spectra of UV pumped LEDs, in which phosphors doped PDMS films were attached to the commercial UV LED, are shown at FIG. 16. The CIE color coordinates and Correlated Color Temperatures (CCTs) are shown at FIG. 17.

A range of "warm" to "cold" white lights was achieved by controlling the blending ratio between the two phosphors. With a blue/yellow weight ratio of 1:1, a white emission with CIE coordinates of (0.32, 0.35), a CCT of 6260 K, and a color-rendering index (CRI) of 75, was obtained.

Figure 18:
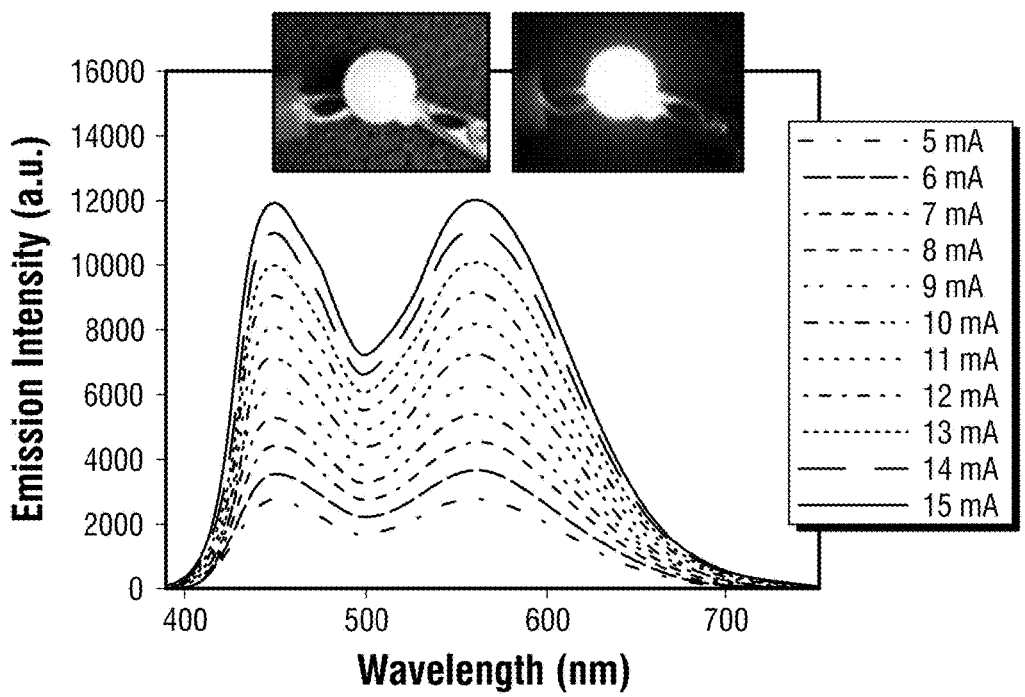
FIG. 18 depicts emission spectra of one embodiment of a UV pumped white light emitting diode at different driving currents.
Figure 19:
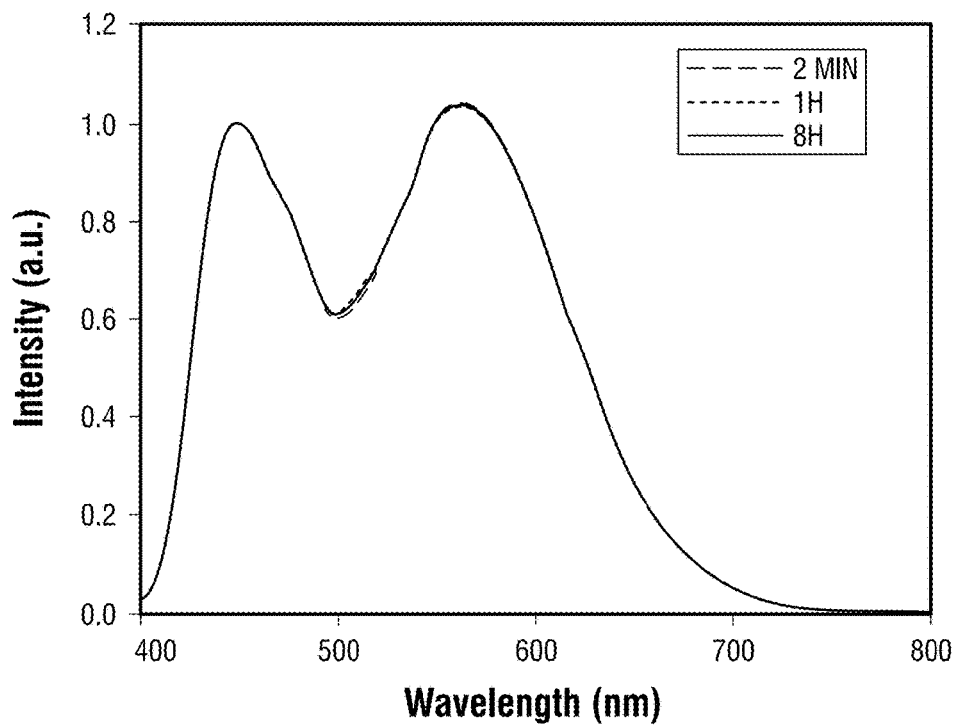
FIG. 19 depicts emission spectra of one embodiment of a UV pumped white light emitting diode operated in air for more than eight hours with a brightness of about 400 cd/m$_2$.

Excellent color stability was observed in this white LED at different operating currents, as shown at FIG. 18. It was believed that this was due to the little-to-no energy transfer from the blue phosphors to the yellow phosphors, as there was a minimum overlap between the excitation of yellow phosphors and the emission of blue phosphors (FIG. 14). The white LED also showed great device stability in air with almost no change of light brightness and color during the preliminary testing, i.e., the device continuously on at ~400 cd/m$^2$ for more than eight hours under the same operating power (FIG. 19).

The blue (BaMgAl$_{10}$O$_{17}$:Eu$^{2+}$) and yellow ((C$_4$N$_2$H$_{14}$)$_4$SnBr$_{10}$) phosphors were blended with Sylgard 184 polydimethylsiloxane (PDMS) encapsulant, and put in a polytetrafluoroethylene (PTFE) mold to control shape and thickness.

The whole mold was heated at 100° C. for 40 min in an oven to cure PDMS. The phosphors doped PDMS films were then attached to a UVTOP® UV LED with window, 340 nm, 0.33 mW (THORLABS) to form UV pumped LEDs. The LEDs were driven by a Keithly 2400 sourcemeter and emission spectra were recorded on an Ocean Optics USB4000 Miniature Fiber Optic Spectrometer. For device stability test, a white light LED was continuously powered by a Keithley 2400 at a stable current power to give a brightness of ~400 cd/m$^2$. Emission spectra were recorded at periodic intervals using an Ocean Optics USB4000 Miniature Fiber Optic Spectrometer.

Example 12—0D Tin Iodide Perovskites

Using the procedures of Examples 1 and 2, a series of 0D tin iodide perovskites were made. The 0D tin iodide perovskites of this example had the following structure:

$$(C_4N_2H_{14})_4[SnI_6]I_4$$

Figure 20:
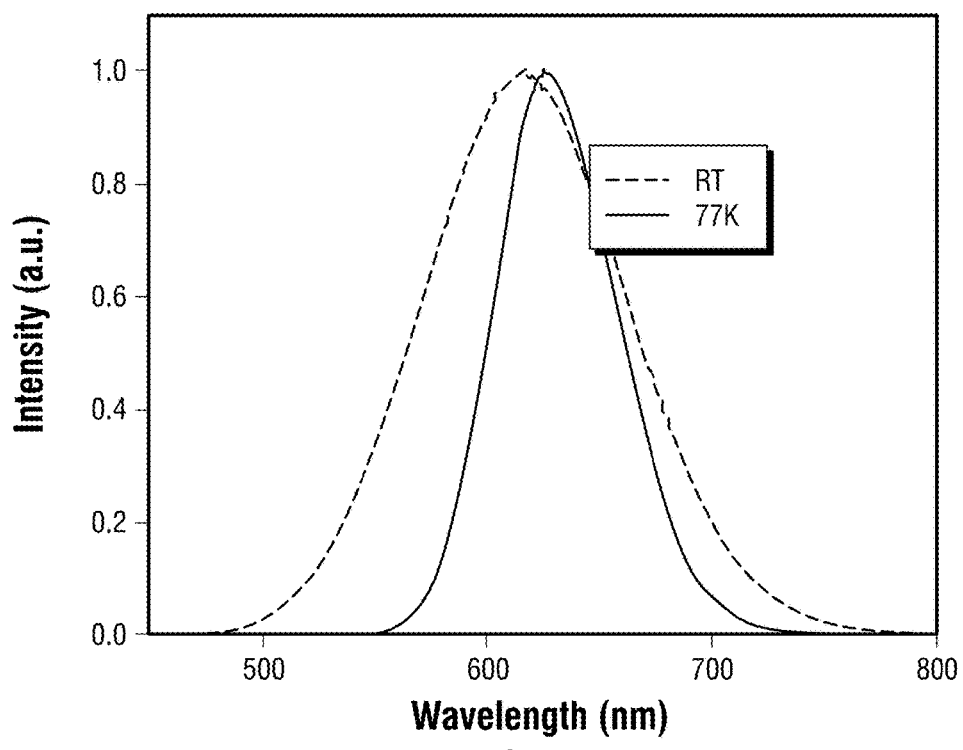
FIG. 20 depicts emission spectra of one embodiment of a 0D tin iodide perovskite.

FIG. 20 shows the emission spectra of the sample of bulk crystals of this example at room temperature (R.T.) and 77 K. The bulk crystals of this example had a largest dimension of about 1 mm, and a thickness of about 0.5 mm. The emission data indicated that the crystals of this example released red light (from 620 to 650 nm), which demonstrated that altering the halide ion was used successfully to tune or change the color of light emitted by the 0D perovskites of Examples 1 and 2, and those of the current example.

While the present invention may be embodied in many different forms, disclosed herein are specific illustrative embodiments thereof that exemplify the principles of the invention. It should be emphasized that the present invention is not limited to the specific embodiments illustrated.

We claim:

1. A metal halide perovskite crystal having a 0D structure, and a unit cell according to formula (I), $$R_a[MX_6]X_d \quad (I);$$

wherein R is an organic ligand comprising (i) a hydrocarbyl substituted with at least one positively charged moiety, or (ii) an aryl substituted with at least one positively charged moiety;

a is 2 to 8;

M is a dication metal atom selected from the group consisting of Sn, Mn, Co, and Ge;

X is a halide ion selected from the group consisting of Cl, Br, and I;

$MX_6$ has an octahedral structure; and d is 2 to 10.

2. The metal halide perovskite of claim 1, wherein the organic ligand is a compound according to formula (A):

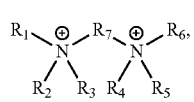

(A)

wherein each of $R_1$-$R_6$ is independently hydrogen or a monovalent $C_1$-$C_{20}$ hydrocarbyl, and $R_7$ is a divalent $C_1$-$C_{20}$ hydrocarbyl or a divalent $C_6$-$C_{20}$ aryl.

3. The metal halide perovskite of claim 2, wherein $R_7$ is a divalent, unsubstituted $C_1$-$C_4$ hydrocarbyl; $R_2$, $R_3$, $R_5$, and $R_6$ are hydrogen; each of $R_1$ and $R_4$ is independently a monovalent, unsubstituted $C_1$-$C_3$ hydrocarbyl, and the organic ligand is a compound according to the following formula (D):

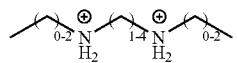

(D)

4. The metal halide perovskite of claim 2, wherein $R_7$ is a divalent, unsubstituted $C_6$ aryl; each of $R_2$, $R_3$, $R_5$, and $R_6$ is hydrogen; each of $R_1$ and $R_4$ is independently a monovalent, unsubstituted $C_1$-$C_3$ hydrocarbyl; and the organic ligand is a compound according to the following formula (G):

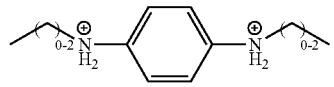

(G)

5. The metal halide perovskite of claim 1, wherein the organic ligand is a compound according to the following formula (H):

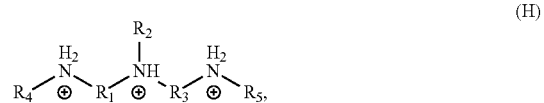

(H)

wherein each of $R_1$ and $R_3$ is independently a divalent $C_1$-$C_{20}$ hydrocarbyl, and each of $R_2$, $R_4$, and $R_5$ is independently hydrogen or a monovalent $C_1$-$C_{20}$ hydrocarbyl.

6. The metal halide of claim 5, wherein $R_2$ is hydrogen; each of $R_4$ and $R_5$ is independently a monovalent, unsubstituted $C_1$-$C_3$ hydrocarbyl; each of $R_1$ and $R_3$ is independently a divalent, unsubstituted $C_2$-$C_4$ hydrocarbyl; and the organic ligand is a compound according to the following formula (I):

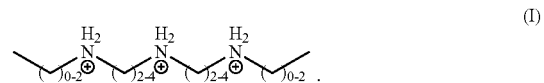

(I)

7. The metal halide of claim 5, wherein $R_2$ is a divalent $C_2$-$C_4$ hydrocarbyl substituted with a secondary amine; each of $R_4$ and $R_5$ is independently a monovalent, unsubstituted $C_1$-$C_3$ hydrocarbyl; each of $R_1$ and $R_3$ is independently a divalent, unsubstituted $C_2$-$C_4$ hydrocarbyl; and the organic ligand is a compound according to the following formula (J):

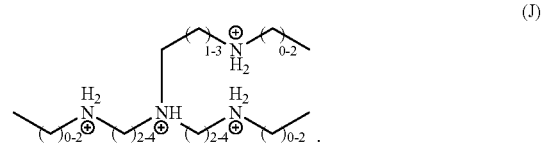

(J)

8. The metal halide perovskite of claim 1, wherein the organic ligand is a compound according to the following formula (K):

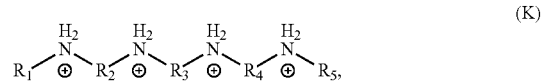

(K)

wherein $R_1$ and $R_5$ are independently a monovalent $C_1$-$C_{20}$ hydrocarbyl or hydrogen, $R_2$ and $R_4$ are independently a divalent $C_1$-$C_{20}$ hydrocarbyl, and $R_3$ is a divalent $C_1$-$C_{20}$ hydrocarbyl or a divalent $C_6$-$C_{20}$ aryl.

9. The metal halide perovskite of claim 8, wherein $R_1$ and $R_5$ are independently an unsubstituted, monovalent $C_1$-$C_3$ hydrocarbyl; $R_2$, $R_3$, and $R_4$ are independently an unsubstituted, divalent $C_2$-$C_4$ hydrocarbyl, and the organic ligand has a structure according to the following formula (L):

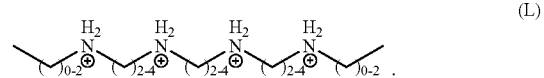

(L)

10. The metal halide perovskite of claim 1, wherein the organic ligand is a compound according to the following formula (M):

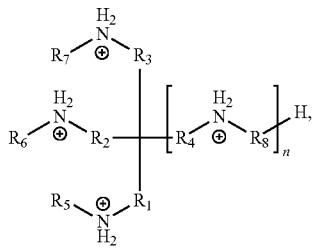
(M)

wherein n is 0 or 1, each of $R_1$-$R_4$ and $R_8$ is independently a divalent $C_1$-$C_{20}$ hydrocarbyl, and each of $R_5$-$R_7$ is independently a monovalent $C_1$-$C_{20}$ hydrocarbyl or hydrogen.

11. The metal halide perovskite of claim 10, wherein n is 1, $R_1$-$R_4$ are independently an unsubstituted, divalent $C_1$-$C_4$ hydrocarbyl; $R_8$ is an unsubstituted, divalent $C_1$-$C_3$ hydrocarbyl; $R_5$-$R_7$ are independently selected from an unsubstituted, monovalent $C_1$-$C_3$ hydrocarbyl; and the organic ligand is a compound according to the following formula (N):

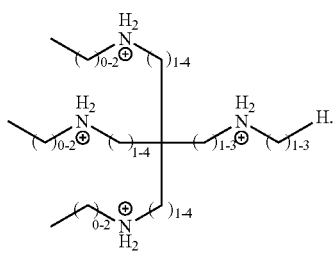
(N)

12. The metal halide perovskite of claim 10, wherein n is 0, $R_1$-$R_3$ are independently an unsubstituted, divalent $C_1$-$C_4$ hydrocarbyl; $R_5$-$R_7$ are independently an unsubstituted, monovalent $C_1$-$C_3$ hydrocarbyl; and the organic ligand is a compound according to the following formula (O):

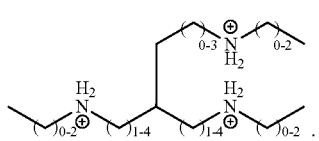
(O)

13. The metal halide perovskite of claim 1, wherein the organic ligand is a compound according to the following formula (P):

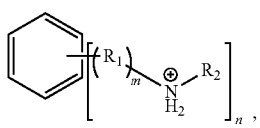
(P)

wherein m is 0 or 1, n is 1-4, each $R_1$ is independently a divalent $C_1$-$C_{20}$ hydrocarbyl, and each $R_2$ is independently a monovalent $C_1$-$C_{20}$ hydrocarbyl or hydrogen.

14. The metal halide perovskite of claim 13, wherein m is 0, n is 3, $R_2$ is independently an unsubstituted, monovalent $C_1$-$C_3$ hydrocarbyl, and the organic ligand is a compound according to the following formula (Q):

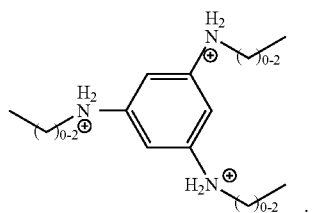
(Q)

15. The metal halide perovskite of claim 1, wherein the organic ligand comprises a compound according to one of structures (1)-(10):

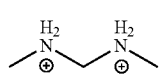
(1)

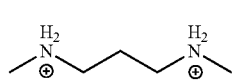
(2)

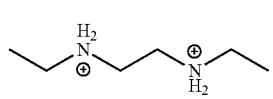
(3)

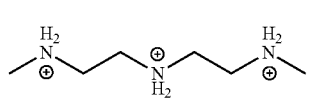
(4)

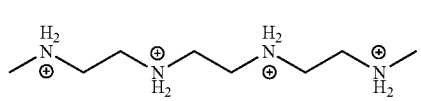
(5)

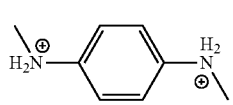
(6)

(7)

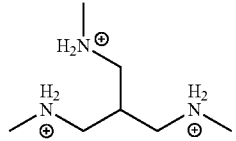
(8)

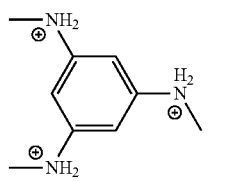
(9)

(10)

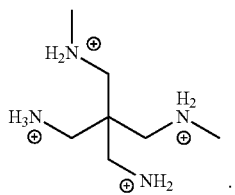

16. The metal halide perovskite of claim 1, wherein the organic ligand is N, N'-dimethylethane-1,2-diammonium:

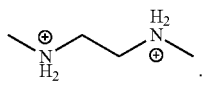

17. The metal halide perovskite of claim 1, wherein the organic ligand is N, N'-dimethylethane-1,2-diammonium; a is 4, M is Sn, X is Br, d is 4, and the unit cell has the following formula:

$(C_4N_2H_{14})_4[SnBr_6]Br_4$.

18. The metal halide perovskite of claim 1, wherein the organic ligand is N, N'-dimethylethane-1,2-diammonium; a is 4, M is Sn, X is I, d is 4, and the unit cell has the following formula:

$(C_4N_2H_{14})_4[SnI_6]I_4$.

19. The metal halide perovskite of claim 1, wherein the photoluminescence quantum efficiency of the crystal is at least 90%.

20. An optoelectronic device comprising the metal halide perovskite of claim 1, wherein the metal halide perovskite is a light emitting material.

21. The device of claim 20, wherein the metal halide perovskite emits light that is blue, green, yellow, orange, or red.

22. The device of claim 20, wherein the metal halide perovskite is a yellow phosphor.

23. The device of claim 22, further comprising a blue phosphor, wherein the blue phosphor and the metal halide perovskite are present in the device as a mixture.

24. The device of claim 20, wherein the device is a white light emitting device.

25. The device of claim 20, wherein the device comprises a full color display.

26. The device of claim 20, wherein the device is a solid-state lighting device.

27. The device of claim 20, wherein the optoelectronic device is a photovoltaic cell, a light emitting diode, a light emitting electrochemical cell, a photodetector, or an optically pumped laser.

* * * * *